United States Patent
Sinha et al.

(10) Patent No.: US 9,402,912 B2
(45) Date of Patent: *Aug. 2, 2016

(54) ANTIBIOTIC CONJUGATES DIRECTLY LINKED WITH STEROID DRUGS

(71) Applicant: Allergan, Inc., Irvine, CA (US)

(72) Inventors: Santosh C. Sinha, Ladera Ranch, CA (US); Ken Chow, Newport Coast, CA (US); Liming Wang, Irvine, CA (US); Michael E. Garst, Newport Beach, CA (US); Mayssa Attar, Placentia, CA (US); Brandon D. Swift, Camarillo, CA (US)

(73) Assignee: Allergan, Inc., Irvine, CA (US)

( * ) Notice: Subject to any disclaimer, the term of this patent is extended or adjusted under 35 U.S.C. 154(b) by 38 days.

This patent is subject to a terminal disclaimer.

(21) Appl. No.: 14/198,939

(22) Filed: Mar. 6, 2014

(65) Prior Publication Data

US 2014/0256612 A1    Sep. 11, 2014

Related U.S. Application Data

(60) Provisional application No. 61/775,161, filed on Mar. 8, 2013.

(51) Int. Cl.

| C07D 405/12 | (2006.01) |
| A61K 47/48 | (2006.01) |
| A61K 9/00 | (2006.01) |
| C07D 215/56 | (2006.01) |
| C07D 401/04 | (2006.01) |
| C07D 471/04 | (2006.01) |
| C07D 498/06 | (2006.01) |

(52) U.S. Cl.
CPC ......... *A61K 47/48115* (2013.01); *A61K 9/0048* (2013.01); *A61K 47/48123* (2013.01); *C07D 215/56* (2013.01); *C07D 401/04* (2013.01); *C07D 405/12* (2013.01); *C07D 471/04* (2013.01); *C07D 498/06* (2013.01)

(58) Field of Classification Search
None
See application file for complete search history.

(56) References Cited

U.S. PATENT DOCUMENTS

| 2,999,102 A | 9/1961 | Heider et al. |
| 3,147,183 A | 9/1964 | Heider et al. |
| 3,916,002 A | 10/1975 | Taubert et al. |
| 4,980,470 A | 12/1990 | Masuzawa et al. |
| 5,565,568 A | 10/1996 | Cho et al. |
| 5,688,792 A | 11/1997 | Barbachyn et al. |
| 5,849,599 A | 12/1998 | Oh et al. |
| 6,051,576 A | 4/2000 | Ashton et al. |
| 6,306,842 B1 | 10/2001 | Lai et al. |
| 7,579,334 B2 | 8/2009 | Mercep |
| 8,268,812 B2 | 9/2012 | Hubschwerlen et al. |
| 2001/0049366 A1 | 12/2001 | Singh et al. |
| 2003/0118528 A1 | 6/2003 | Walters et al. |
| 2005/0085413 A1 | 4/2005 | Jin et al. |
| 2006/0105941 A1 | 5/2006 | Schiffman et al. |
| 2010/0063017 A1 | 3/2010 | Rajan |
| 2012/0046461 A1* | 2/2012 | Hanson ............ A61K 47/48115 540/108 |
| 2014/0256612 A1 | 9/2014 | Sinha et al. |
| 2014/0256651 A1 | 9/2014 | Sinha et al. |
| 2014/0256658 A1 | 9/2014 | Sinha et al. |
| 2014/0256660 A1 | 9/2014 | Sinha et al. |
| 2014/0256666 A1 | 9/2014 | Sinha et al. |
| 2014/0256694 A1 | 9/2014 | Sinha et al. |
| 2014/0256696 A1 | 9/2014 | Sinha et al. |

FOREIGN PATENT DOCUMENTS

| EP | 0659763 A2 | 6/1995 |
| WO | 9520567 A1 | 8/1995 |
| WO | 0105819 A1 | 1/2001 |
| WO | 02087586 A1 | 11/2002 |
| WO | WO03031441 A1 | 4/2003 |
| WO | WO03031443 A1 | 4/2003 |
| WO | 03043657 A1 | 5/2003 |
| WO | WO03032962 A3 | 7/2003 |
| WO | 2004-112838 | 12/2004 |
| WO | 2008094507 A2 | 8/2008 |
| WO | 2009-109501 | 9/2009 |
| WO | 2010-113151 A1 | 10/2010 |
| WO | 2013-040441 | 3/2013 |
| WO | 2014138343 A1 | 9/2014 |
| WO | 2014138350 A1 | 9/2014 |
| WO | 2014138359 A1 | 9/2014 |
| WO | 2014138375 A1 | 9/2014 |
| WO | 2014138403 A1 | 9/2014 |
| WO | 2014138425 A1 | 9/2014 |
| WO | 2014138437 A1 | 9/2014 |
| WO | WO2014138343 A1 | 9/2014 |
| WO | WO2014138375 A1 | 9/2014 |
| WO | WO2014138403 A1 | 9/2014 |

OTHER PUBLICATIONS

Salunke, Current Medicinal Chemistry, 2006, 13, 813-847.*
Ding, 2004, Organic letters, 6, 3433-3436.*
Bucki, Antimicrobial Agents and Chemotherapy, Jun. 2010, p. 2525-2533.*
Figuerova, Rev Latinoam Microbiol, 2008, 50(1-2), 13-18.*
Bremner, John B.; Ambrus, Joseph I.; Samosorn, Siritron, Dual action-based approaches to antibacterial agents, Current Medicinal Chemistry, 2007, 1459-1477, 14(13).
Cross, L.C. et al, Rules for the Nomenclature of Organic Chemistry, Section E: Stereochemistry, Pure & Appl. Chem., 1976, 11-30, 45.
Heinrich Stahl, Pharmaceutical Salts, Handbook of Pharmaceutical Salts, 2002, 329-345, International Union of Pure and Applied Chemistry, Verlag Helvetica Chemica Acta- Zürich.

(Continued)

*Primary Examiner* — Satyanarayana R Gudibande
(74) *Attorney, Agent, or Firm* — Barbara C. Potts

(57) ABSTRACT

The present invention describes novel single drug entities, formed by direct linkage of an antibiotic to a steroidal drug. Upon topical application to the eye, the conjugate would undergo enzymatic and/or hydrolytic cleavage to release the individual drugs. The antibiotic is coupled directly to the steroid drug.

9 Claims, 2 Drawing Sheets

(56) References Cited

OTHER PUBLICATIONS

Macky, et al., Synthesis, Pharmacokinetics, Efficacy, and Rat Retinal Toxicity of a Novel Mitomycin C-Triamcinolone Acetonide Conjugate, Journal of Medicinal Chemistry 2002, 1122-1127, 45, American Chemical Society.

N. Das et al., Codrug: An efficient approach for drug optimization, Codrug: an efficient approach for drug optimization, 2010, 571-588, 41, European Journal of Pharmaceutical Sciences.

Philip R Hamann, An Anti-CD33 Antibody-Calicheamicin Conjugate for Treatment of Acute Myeloid Leukemia. Choice of Linker, 2002.

Pokrovskaya, Varvara; Baasov, Timor, Dual-acting hybrid antibiotics: a promising strategy to combat bacterial resistance, Expert Opinion on Drug Discovery, 2010, 883-902, 5(9).

Yang et al, An Intravitreal Sustained-Release Triamcinolone and 5-Fluorouracil Codrug in the Treatment of Experimental Proliferative Vitreoretinopathy, Arch Ophthalmology, 1998, 69-77, 116.

Yong et al, In Vitro Activities of DA-7867, a Novel Oxazolidinone, against Recent Clinical Isolates of Aerobic and Anaerobic Bacteria, Antimicrobial Agents and Chemotherapy, Jan. 2004, 352-357, vol. 48, No. 1.

Hubschwerlen et al., Design, Synthesis and Biological Evaluation of Oxazolidinone—Quinolone Hybrids, Bioorganic & Medicinal Chemistry 11, 2003, 2313-2319.

Hubschwerlen et al., Structure—Activity Relationship in the Oxazolidinone—Quinolone Hybrid Series: Influence of the Central Spacer on the Antibacterial Activity and the Mode of Action, Bioorganic & Medicinal Chemistry Letters 13, 2003, 4229-4233.

Singh et al, Mutual Prod rugs—A Recent Trend in Prodrug Design, Indian Journal of Pharmaceutical Science, 1994, 56(3), pp. 69-79.

Leppänen et al., Design and Synthesis of a Novel L-Dopa-Entacapone Codrug, Journal of Medicinal Chemistry, 2002, vol. 45, No. 6, 1379-1382.

Petersen et al., Comparative In Vitro Activities of AC98-6446, a Novel Semisynthetic Glycopeptide Derivative of the Natural Product Mannopeptimycin α, and Other Antimicrobial Agents against Gram-Positive Clinical Isolates, Antimicrobial Agents and Chemotherapy, Mar. 2004, p. 739-746, vol. 48, No. 3.

Menger et al., Synthesis and Reactivity of 5-Fluorouracil/Cytarabine Mutual Prodrugs, J. Org. Chem. 1997, 62, 9083-9088.

Vera-Cabrera et al., In Vitro Activities of New Quinolones and Oxazolidinones against Actinomadura madurae, Antimicrobial Agents and Chemotherapy, Mar. 2004, p. 1037-1039, vol. 48, No. 3.

Vera-Cabrera et al., In Vitro Activities of New Antimicrobials against Nocardia brasiliensis, Antimicrobial Agents and Chemotherapy, Feb. 2004, p. 602-604, vol. 48, No. 2.

Nudelman et al., Novel Mutual Prodrug of Retinoic and Butyric Acids with Enhanced Anticancer Activity, Journal of Medicinal Chemistry, 2000, vol. 43, No. 15, 2962-2966.

Anderegg et al., (The Quality Control Working Group) Quality Control Guidelines for MIC Susceptibility Testing of Omiganan Pentahydrochloride (MBI 226), a Novel Antimicrobial Peptide, Journal of Clinical Microbiology, Mar. 2004, p. 1386-1387, vol. 42, No. 3.

Sanchez et al., The Synthesis, Structure-Activity, and Structure-Side Effect Relationships of a Series of 8-Alkoxy- and 5-Amino-8-alkoxyquinolone Antibacterial Agents, Journal of Medicinal Chemistry, 1995, vol. 38. No. 22, 3478-4487.

Donnenfeld, Eric et al, Topical Ophthalmic Cyclosporine: Pharmacology and Clinical Uses, Survey of Ophthalmology, Jun. 2009, 321-338, 54(3).

Towler, H.M.A. et al, Combination Low Dose Cyclosporin A and Steroid Therapy in Chronic Intraocular Inflammation, Eye, Jan. 1990, 514-520, 4.

Hamilton-Miller, J.M.T., Dual-Action Antibiotic Hybrids, Journal of Antimicrobial Chemotherapy, Jan. 1994, 197-200, 33(2).

Michael, Katja et al, Enhanced RNA Binding of Dimerized Aminoglycosides, Bioorganic & Medicinal Chemistry, 1999, 1361-1371, 7.

Belfort, Rubens et al, Safety and Efficacy of Moxifloxacin-Dexamethasone Eyedrops as Treatment for Bacterial Ocular Infection Associated with Bacterial Blepharitis, Adv Ther, 2012, 416-426, 29(5).

Shulman, D.G. et al, Comparative Evaluation of the Short-Term Bactericidal Potential of a Steroid-Antibiotic Combination Versus Steroid in the Treatment of Chronic Bacterial Blepharitis and Conjunctivitis, European Journal of Ophthalmology, 1996, 361-367, 6(4).

Patent Cooperation Treaty, Notification of Transmittal of the Int'l Search Report & the Written Opinion of the Int'l Searching Authority, or Declaration, 061314, pp. 9.

Patent Cooperation Treaty, Notification of Transmittal of the International Search Report & The Written Opinion of the Int'l Searching Authority, or the Declaration, PCT/US2014/021283, Jun. 2, 2014, pp. 11.

Patent Cooperation Treaty, Notification of Transmittal of the International Search Report & The Written Opinion of the Int'l Searching Authority, or the Declaration, PCT/US2014/021283, Jun. 3, 2014, pp. 11.

* cited by examiner

ANTIBIOTIC CONJUGATES DIRECTLY LINKED WITH STEROID DRUGS

RELATED APPLICATIONS

This application claims the benefit of U.S. Provisional Patent Application Ser. No. 61/775,161 filed Mar. 8, 2013, the disclosure of which is hereby incorporated in its entirety herein by reference.

FIELD OF THE INVENTION

The present invention describes novel single drug entities, formed by direct linkage of an antibiotic to a steroidal drug. Upon topical application to the eye, the single drug entity would undergo enzymatic and/or hydrolytic cleavage to release the individual drugs. The antibiotic moiety is coupled directly to the steroid moiety.

SUMMARY OF THE INVENTION

Due to increasing bacterial resistance to antibiotics, there is a constant need for antibiotic compounds. A conjugate drug, also referred to as a co-drug, a pro-drug, or a hybrid drug, comprises two or more different or same drugs within one single chemical entity wherein each drug contains an appropriate chemical functionality to enable them to be connected directly, which is cleavable and biologically labile.

The antibiotic moiety and the steroid moiety, of the hybrid compounds disclosed herein are connected to each other via covalent bonds, such that said bond degrades in vivo to yield the respective antibiotic and the respective steroid. Each bond is an amide bond or an ester bond depending on the nature of the bonding site.

By appropriate structural design, it may be possible to control the release of each drug. When the drugs are chemically combined, the resulting hybrid will usually have different physicochemical properties compared to the individual parent drugs, which may provide superior properties for delivery when compared to delivery of a physical mixture of the drugs.

Degradation of these covalent bonds generally, yields the corresponding acid, or alcohol by hydrolysis or by a related reaction. A compound which degrades in vivo yields the active steroid drug and the active antibiotic drug at some point in the metabolic process of the claimed compound. In many cases, cleavage of the first ester bond will release one active, and cleavage of the second ester bond will release the second active.

DETAILED DESCRIPTION OF THE INVENTION

Figure 1:
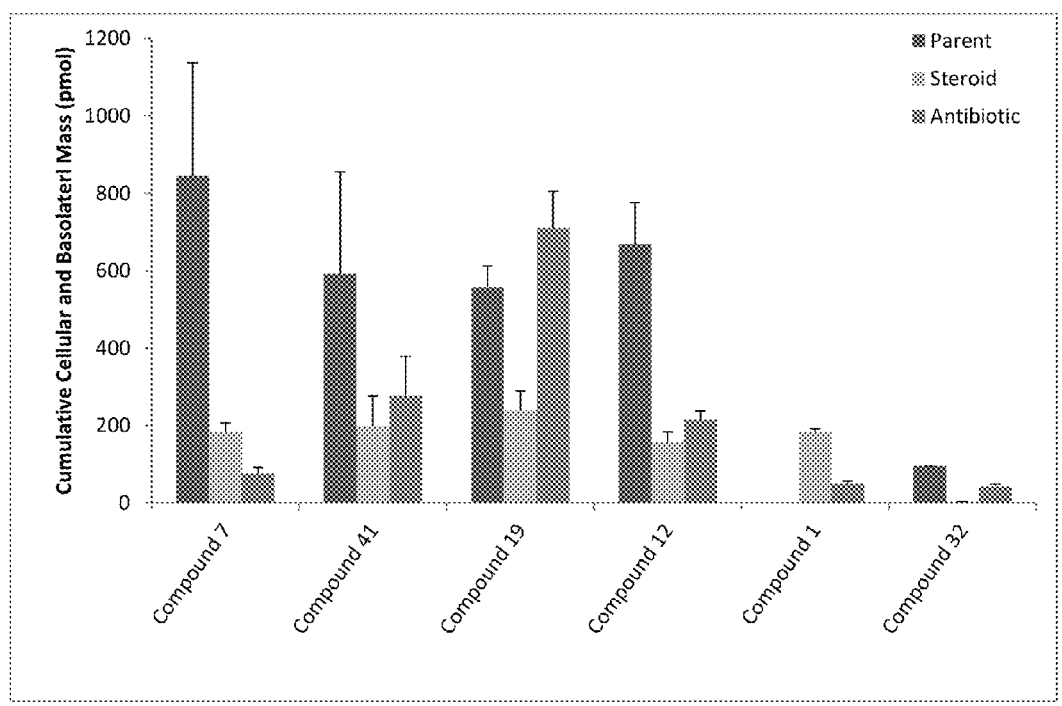
FIG. 1 Shows the cellular uptake of ester linked hybrid (parent) compounds and the hydrolyzed metabolites (steroid and antibiotic) after a two hour incubation with Human Corneal Epithelial Cells.

The hybrid drugs of the invention provide a unique delivery of an antibiotic and a steroid for the treatment and prevention of ophthalmic bacterial infections and anti-inflammatory conditions. A single drug entity is advantageous to individual dosing of each drug because of the ability for simultaneous dosing and elimination of washout concerns when applying each drug separately.

The hybrid drugs of the invention have anti-bacterial activity and anti-inflammatory activity and are very useful compounds capable of producing the effect of an antibacterial drug and an anti-inflammatory drug with a broad range of activity in monotherapy.

The use of an antibiotic/steroid hybrid drug is indicated where the risk of infection is high or where there is an expectation that potentially dangerous numbers of bacteria will be present in the eye. The anti-inflammatory component of the composition is useful in treating inflammation associated with physical trauma to ophthalmic tissues, inflammation associated with bacterial infections and inflammation resulting from surgical procedures. The combination of an antibiotic and steroid is also useful in post-operative inflammation where there is an increased chance of bacterial infection. The composition of the invention may also be used prophylactically in connection with various ophthalmic surgical procedures that create a risk of bacterial infection. Other examples of ophthalmic conditions which may be treated with the compositions of the present invention include infective conditions with associated inflammation and where the use of steroids is acceptable; such conditions may include, but not limited to conjunctivitis, keratitis, blepharitis, endophthalmitis, dacryocystitis, hordeolum, corneal ulcers, anterior blepharitis, posterior blepharitis, meibomian gland dysfunction, dry eye disease (keratoconjunctivitis sicca) ocular pain, ocular pain and inflammation post-ocular surgery, bacterial conjunctivitis, anterior uveitis, post-surgical inflammation, inflammatory conditions of the palpebral and bulbar conjunctiva, cornea, and anterior segment of the globe, such as allergic conjunctivitis, ocular rosacea, dry eye, blepharitis, endophthalmitis, meibomian gland dysfunction, superficial punctate keratitis, herpes zoster keratitis, iritis, cyclitis, selected infective conjunctivitis, corneal injury from chemical radiation, or thermal burns, penetration of foreign bodies, allergy, and combinations thereof.

The present invention relates to hybrid drugs comprising at one antibiotic moiety and one steroid moiety, or a pharmaceutical salt thereof, which are separately connected via a covalent bond to each other such that said covalent bonds degrade in vivo to yield the respective antibiotic and steroid independently.

In another aspect, the present invention relates to hybrid drugs, which degrade in vivo into an antibiotic and a steroidal drug.

In another aspect, the present invention relates to hybrid drugs having two bonds, wherein said bonds are asymmetrically degraded in vivo to release the two independent drugs: an antibiotic and a steroidal drug.

The hybrid drugs disclosed herein comprise antibiotics moieties belonging to distinct classes: fluoroquinolones, cephalosporins, chloramphenicol, aminoglycosides, penicillins, erythromycin, macrolide antibiotics and oxazolidinones.

Fluoroquinolones include, but are not limited to: levofloxacin, moxifloxacin, gatifloxacin, gemifloxacin, trovafloxacin, ofloxacin, ciprofloxacin, sparfloxacin, grepafloxacin, norfloxacin, enoxacin, lomefloxacin, fleroxacin, tosufloxacin, prulifloxacin, pazufloxacin, clinafloxacin, garenoxacin, and sitafloxacin.

Cephalosporins include, but are not limited to: loracarbef, cephalexin, cefuroxime, ceftriaxone, cefotaxime, ceftizoxime, ceftibuten, ceftazidime, cefprozil, cefpodoxime, cefoxitin, cefotetan, cefotaxime, cefoperazone, cefixime, cefepime, cefditoren, cefdinir, cefoperaxone, moxalactam, cefazolin, cefamandole, cefadroxil, cefaclor, cephalothin, cephradine, cephacetrile, and cephalothin.

Aminoglycosides include, but are not limited to: tobramycin, streptomycin, gentamicin, kanamycin, amikacin and netilmicin.

Penicillins include, but are not limited to: penicillin G, ticarcillin, methicillin, phenethicillin, cloxacillin, dicloxacillin, nafcillin, oxacillin.

Macrolide antibiotics include, but are not limited to: erythromycin and azithromycin.

Oxazolidinones include, but are not limited to: linezolid.

In another embodiment the compounds disclosed herein comprise at least two antibiotic drug moieties selected from levofloxacin, moxifloxacin, gatifloxacin, gemifloxacin, trovafloxacin, ofloxacin, ciprofloxacin, sparfloxacin, grepafloxacin, norfloxacin, enoxacin, lomefloxacin, fleroxacin, tosufloxacin, prulifloxacin, pazufloxacin, clinafloxacin, garenoxacin, sitafloxacin, loracarbef, cephalexin, cefuroxime, ceftriaxone, ceftaxime, ceftizoxime, ceftibuten, ceftazidime, cefprozil, cefpodoxime, cefoxitin, cefotetan, cefotaxime, cefoperazone, cefixime, cefepime, cefditoren, cefdinir, cefoperaxone, moxalactam, cefazolin, cefamandole, cefadroxil, cefaclor, cephalothin, cephradine, cephacetrile, cephalothin, chloramphenicol, tobramycin, streptomycin, gentamicin, kanamycin, amikacin, netilmicin, penicillin g, ticarcillin, methicillin, phenethicillin, cloxacillin, dicloxacillin, nafcillin, oxacillin, erythromycin and azithromycin.

In another embodiment the hybrid compounds disclosed herein comprise a steroidal moiety selected from: dexamethasone, betamethasone, triamcinolone acetonide, prednisolone and hydrocortisone.

In another embodiment the compounds disclosed herein comprise at least one antibiotic moiety selected from levofloxacin, moxifloxacin, gatifloxacin, gemifloxacin, trovafloxacin, ofloxacin, ciprofloxacin, sparfloxacin, grepafloxacin, norfloxacin, enoxacin, lomefloxacin, fleroxacin, tosufloxacin, prulifloxacin, pazufloxacin, clinafloxacin, garenoxacin, sitafloxacin, loracarbef, cephalexin, cefuroxime, ceftriaxone, ceftaxime, ceftizoxime, ceftibuten, ceftazidime, cefprozil, cefpodoxime, cefoxitin, cefotetan, cefotaxime, cefoperazone, cefixime, cefepime, cefditoren, cefdinir, cefoperaxone, moxalactam, cefazolin, cefamandole, cefadroxil, cefaclor, cephalothin, cephradine, cephacetrile, cephalothin, chloramphenicol, tobramycin, streptomycin, gentamicin, kanamycin, amikacin, netilmicin, penicillin g, ticarcillin, methicillin, phenethicillin, cloxacillin, dicloxacillin, nafcillin and oxacillin; and at least one steroidal moiety selected from: dexamethasone, betamethasone, triamcinolone acetonide, prednisolone and hydrocortisone.

In another embodiment the hybrid compounds disclosed herein comprise a pro-drug moiety and at least one antibiotic moiety selected from levofloxacin, moxifloxacin, gatifloxacin, gemifloxacin, trovafloxacin, ofloxacin, ciprofloxacin, sparfloxacin, grepafloxacin, norfloxacin, enoxacin, lomefloxacin, fleroxacin, tosufloxacin, prulifloxacin, pazufloxacin, clinafloxacin, garenoxacin, sitafloxacin, loracarbef, cephalexin, cefuroxime, ceftriaxone, cefaxime, ceftizoxime, ceftibuten, ceftazidime, cefprozil, cefpodoxime, cefoxitin, cefotetan, cefotaxime, cefoperazone, cefixime, cefepime, cefditoren, cefdinir, cefoperaxone, moxalactam, cefazolin, cefamandole, cefadroxil, cefaclor, cephalothin, cephradine, cephacetrile, cephalothin, chloramphenicol, tobramycin, streptomycin, gentamicin, kanamycin, amikacin, netilmicin, penicillin g, ticarcillin, methicillin, phenethicillin, cloxacillin, dicloxacillin, nafcillin and oxacillin.

In another embodiment the hybrid compounds disclosed herein comprise one pro-drug moiety and at least one antibiotic moiety selected from levofloxacin, moxifloxacin, gatifloxacin, gemifloxacin, trovafloxacin, ofloxacin, ciprofloxacin, sparfloxacin, grepafloxacin, norfloxacin, enoxacin, lomefloxacin, fleroxacin, tosufloxacin, prulifloxacin, pazufloxacin, clinafloxacin, garenoxacin, sitafloxacin, loracarbef, cephalexin, cefuroxime, ceftriaxone, ceftaxime, ceftizoxime, ceftibuten, ceftazidime, cefprozil, cefpodoxime, cefoxitin, cefotetan, cefotaxime, cefoperazone, cefixime, cefepime, cefditoren, cefdinir, cefoperaxone, moxalactam, cefazolin, cefamandole, cefadroxil, cefaclor, cephalothin, cephradine, cephacetrile, cephalothin, chloramphenicol, tobramycin, streptomycin, gentamicin, kanamycin, amikacin, netilmicin, penicillin g, ticarcillin, methicillin, phenethicillin, cloxacillin, dicloxacillin, nafcillin and oxacillin; and one steroid moiety selected from: dexamethasone, betamethasone, triamcinolone acetonide, prednisolone and hydrocortisone.

In another aspect the invention provides a method comprising administrating to an eye of a mammal a pharmaceutical composition comprising a therapeutically active amount of a hybrid drug comprising at least one antibiotic moieties and one steroid moiety, which are connected via two separate covalent bonds wherein said covalent bonds degrade in vivo to yield the antibiotic and the steroid, wherein each bond is an ester bond or an amide bond, wherein said method is effective in the treatment of a bacterial infection or an inflammation affecting said eye.

In another aspect the invention provides a method according, wherein the bacterial infection is selected from: conjunctivitis, keratitis, blepharitis, dacryocystitis, hordeolum, corneal ulcers, anterior blepharitis, posterior blepharitis, endophthalmitis, meibomian gland dysfunction, dry eye disease (keratoconjunctivitis sicca) ocular pain, ocular pain and inflammation post-ocular surgery, bacterial conjunctivitis, anterior uveitis, post-surgical inflammation, inflammatory conditions of the palpebral and bulbar conjunctiva, cornea, and anterior segment of the globe, such as allergic conjunctivitis, ocular rosacea, blepharitis, meibomian gland dysfunction, superficial punctate keratitis, herpes zoster keratitis, iritis, cyclitis, selected infective conjunctivitis, corneal injury from chemical radiation, or thermal burns, penetration of foreign bodies and allergy.

In another aspect the invention provides a method comprising administrating to an eye of a human a pharmaceutical composition comprising a therapeutically active amount of a hybrid drug comprising at least one antibiotic moieties and one steroid moiety, which are connected via a covalent bond wherein said covalent bond degrades in vivo to yield the antibiotic and the steroid, wherein each bond is an ester bond or an amide bond, wherein said method is effective in the treatment of a bacterial infection or an inflammation affecting said eye.

In another aspect the invention provides a pharmaceutical composition comprising a hybrid drug comprising an antibiotic moiety and a steroid, which are connected via two separate covalent bonds to each other, that said covalent bonds degrade in vivo to yield the antibiotic moiety and the steroid moiety, and wherein each bond is an ester bond or an amide bond, and wherein said pharmaceutical composition is formulated for topical ophthalmic administration.

Depending of the bond formation site, the antibiotic moiety can be linked via an ester bond to the steroid moiety, as shown in the following scheme:

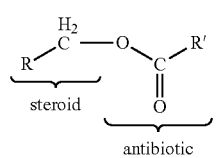

Further the compounds disclosed herein comprise a pro-drug moiety selected from Table 1:

TABLE 1

| Pro-drug Structure | Pro-drug Number |
|---|---|
|  | P1 |
|  | P2 |
|  | P3 |
|  | P4 |
|  | P5 |
|  | P6 |
|  | P7 |

TABLE 1-continued

| Pro-drug Structure | Pro-drug Number |
|---|---|
|  | P8 |
|  | P9 |
|  | P10 |
|  | P11 |
|  | P12 |
|  | P13 |
|  | P14 |
|  | P15 |

Compounds of the invention are shown in Table 2:

TABLE 2

| Compound No. | IUPAC name |
|---|---|
| 1 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate |

TABLE 2-continued

| Compound No. | IUPAC name |
|---|---|
| 2 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-{3-methyl-4-[(5-methyl-2-oxo-1,3-dioxol-4-yl)methyl]piperazin-1-yl}-4-oxo-1,4-dihydroquinoline-3-carboxylate |
| 3 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-(4-{[(acetyloxy)methoxy]carbonyl}-3-methylpiperazin-1-yl)-1-cyclopropyl-6-fluoro-8-methoxy-4-oxo-1,4-dihydroquinoline-3-carboxylate |
| 4 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-(4-{[1-(acetyloxy)ethoxy]carbonyl}-3-methylpiperazin-1-yl)-1-cyclopropyl-6-fluoro-8-methoxy-4-oxo-1,4-dihydroquinoline-3-carboxylate |
| 5 | 2-[(8R,9S,10R,11R,13R,14R,16R,17S)-17-(acetyloxy)-9-fluoro-11-hydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate |
| 6 | 2-[(8R,9S,10R,11R,13R,14R,16R,17S)-17-(butanoyloxy)-9-fluoro-11-hydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate |
| 57 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-[4-(tert-butoxycarbonyl)-3-methylpiperazin-1-yl]-1-cyclopropyl-6-fluoro-8-methoxy-4-oxo-1,4-dihydroquinoline-3-carboxylate |
| 7 | 2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate |
| 8 | 2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-{3-methyl-4-[(5-methyl-2-oxo-1,3-dioxol-4-yl)methyl]piperazin-1-yl}-4-oxo-1,4-dihydroquinoline-3-carboxylate |
| 9 | 2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-(4-{[1-(acetyloxy)ethoxy]carbonyl}-3-methylpiperazin-1-yl)-1-cyclopropyl-6-fluoro-8-methoxy-4-oxo-1,4-dihydroquinoline-3-carboxylate |
| 10 | 2-[(8R,9S,10R,11R,13R,14R,16S,17S)-17-(butanoyloxy)-9-fluoro-11-hydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate |
| 11 | 2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methyl-4-{[(5-methyl-2-oxo-1,3-dioxol-4-yl)methoxy]carbonyl}piperazin-1-yl)-4-oxo-1,4-dihydroquinoline-3-carboxylate |
| 56 | 2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-[4-(tert-butoxycarbonyl)-3-methylpiperazin-1-yl]-1-cyclopropyl-6-fluoro-8-methoxy-4-oxo-1,4-dihydroquinoline-3-carboxylate |
| 12 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate |
| 13 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-{3-methyl-4-[(5-methyl-2-oxo-1,3-dioxol-4-yl)methyl]piperazin-1-yl}-4-oxo-1,4-dihydroquinoline-3-carboxylate |
| 14 | 2-[(8R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-(4-{[(acetyloxy)methoxy]carbonyl}-3-methylpiperazin-1-yl)-1-cyclopropyl-6-fluoro-8-methoxy-4-oxo-1,4-dihydroquinoline-3-carboxylate |

TABLE 2-continued

| Compound No. | IUPAC name |
| --- | --- |
| 15 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-(4-{[1-(acetyloxy)ethoxy]carbonyl}-3-methylpiperazin-1-yl)-1-cyclopropyl-6-fluoro-8-methoxy-4-oxo-1,4-dihydroquinoline-3-carboxylate |
| 16 | 2-[(8R,10S,11R,13R,14R,17S)-17-(butanoyloxy)-11-hydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate |
| 17 | 2-{(8R,10S,11R,13R,14R,17S)-11-hydroxy-10,13-dimethyl-3-oxo-17-[(phenylcarbonyl)oxy]-6,7,8,9,10,11,12,13,14,15,16,17-dodecahydro-3H-cyclopenta[a]phenanthren-17-yl}-2-oxoethyl rel-1-cyclopropyl-6-fluoro-8-methoxy-7-(3-methylpiperazin-1-yl)-4-oxo-1,4-dihydroquinoline-3-carboxylate |
| 18 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methyl-4-{[(5-methyl-2-oxo-1,3-dioxol-4-yl)methoxy]carbonyl}piperazin-1-yl)-4-oxo-1,4-dihydroquinoline-3-carboxylate |
| 47 | 2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-[4-(2-amino-3-methylbutanoyl)-3-methylpiperazin-1-yl]-1-cyclopropyl-6-fluoro-8-methoxy-4-oxo-1,4-dihydroquinoline-3-carboxylate |
| 48 | rel-(2R)-2-amino-4-{4-[1-cyclopropyl-3-({2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethoxy}carbonyl)-6-fluoro-8-methoxy-4-oxo-1,4-dihydroquinolin-7-yl]-2-methylpiperazin-1-yl}-4-oxobutanoic acid |
| 49 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-(4-{2-[(2-amino-3-methylbutanoyl)amino]-3-methylbutanoyl}-3-methylpiperazin-1-yl)-1-cyclopropyl-6-fluoro-8-methoxy-4-oxo-1,4-dihydroquinoline-3-carboxylate |
| 50 | rel-2-amino-5-{[({4-[1-cyclopropyl-3-({2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethoxy}carbonyl)-6-fluoro-8-methoxy-4-oxo-1,4-dihydroquinolin-7-yl]-2-methylpiperazin-1-yl}carbonyl)oxy]methoxy}-5-oxopentanoic acid |
| 51 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-(4-{[({2-[(2-amino-3-methylbutanoyl)amino]-3-methylbutanoyl}oxy)methoxy]carbonyl}-3-methylpiperazin-1-yl)-1-cyclopropyl-6-fluoro-8-methoxy-4-oxo-1,4-dihydroquinoline-3-carboxylate |
| 54 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-[4-(tert-butoxycarbonyl)-3-methylpiperazin-1-yl]-1-cyclopropyl-6-fluoro-8-methoxy-4-oxo-1,4-dihydroquinoline-3-carboxylate |
| 19 | 2-[(8R,9R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate |
| 20 | 2-[(8R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-1-cyclopropyl-6-fluoro-8-methoxy-7-{3-methyl-4-[(5-methyl-2-oxo-1,3-dioxol-4-yl)methyl]piperazin-1-yl}-4-oxo-1,4-dihydroquinoline-3-carboxylate |
| 21 | 2-[(10R,11S,13S,17R)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-7-(4-{[1-(acetyloxy)ethoxy]carbonyl}-3-methylpiperazin-1-yl)-1-cyclopropyl-6-fluoro-8-methoxy-4-oxo-1,4-dihydroquinoline-3-carboxylate |
| 22 | 2-{(8R,10S,11R,13R,14R,17S)-11-hydroxy-10,13-dimethyl-3-oxo-17-[(phenylcarbonyl)oxy]-2,3,6,7,8,9,10,11,12,13,14,15,16,17-tetradecahydro-1H-cyclopenta[a]phenanthren-17-yl}-2-oxoethyl rel-1-cyclopropyl-6-fluoro-8-methoxy-7-(3-methylpiperazin-1-yl)-4-oxo-1,4-dihydroquinoline-3-carboxylate |
| 23 | 2-{(8R,9R,10S,11R,13R,14R,17S)-11-hydroxy-10,13-dimethyl-3-oxo-17-[(phenylcarbonyl)oxy]-2,3,6,7,8,9,10,11,12,13,14,15,16,17-tetradecahydro-1H-cyclopenta[a]phenanthren-17-yl}-2-oxoethyl rel-7-(4-{[1-(acetyloxy)ethoxy]carbonyl}-3-methylpiperazin-1-yl)-1-cyclopropyl-6-fluoro-8-methoxy-4-oxo-1,4-dihydroquinoline-3-carboxylate |

TABLE 2-continued

| Compound No. | IUPAC name |
|---|---|
| 55 | 2-[(8R,9R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-7-[4-(tert-butoxycarbonyl)-3-methylpiperazin-1-yl]-1-cyclopropyl-6-fluoro-8-methoxy-4-oxo-1,4-dihydroquinoline-3-carboxylate |
| 24 | 2-[(4aR,4bS,5R,6aR,6bR,9aS,10aR,10bR)-4b-fluoro-5-hydroxy-4a,6a,8,8-tetramethyl-2-oxo-2,4a,4b,5,6,6a,9a,10,10a,10b,11,12-dodecahydro-6bH-naphtho[2',1':4,5]indeno[1,2-d][1,3]dioxol-6b-yl]-2-oxoethyl rel-7-(4-{[1-(acetyloxy)ethoxy]carbonyl}-3-methylpiperazin-1-yl)-1-cyclopropyl-6-fluoro-8-methoxy-4-oxo-1,4-dihydroquinoline-3-carboxylate |
| 25 | 2-[(4aR,4bS,5R,6aR,6bR,9aS,10aR,10bR)-4b-fluoro-5-hydroxy-4a,6a,8,8-tetramethyl-2-oxo-2,4a,4b,5,6,6a,9a,10,10a,10b,11,12-dodecahydro-6bH-naphtho[2',1':4,5]indeno[1,2-d][1,3]dioxol-6b-yl]-2-oxoethyl rel-1-cyclopropyl-6-fluoro-8-methoxy-7-{3-methyl-4-[(5-methyl-2-oxo-1,3-dioxol-4-yl)methyl]piperazin-1-yl}-4-oxo-1,4-dihydroquinoline-3-carboxylate |
| 26 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-[(4aS,7aS)-octahydro-6H-pyrrolo[3,4-b]pyridin-6-yl]-4-oxo-1,4-dihydroquinoline-3-carboxylate |
| 27 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-{1-[(5-methyl-2-oxo-1,3-dioxol-4-yl)methyl]octahydro-6H-pyrrolo[3,4-b]pyridin-6-yl}-4-oxo-1,4-dihydroquinoline-3-carboxylate |
| 28 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-[(4aS,7aS)-1-{[(acetyloxy)methoxy]carbonyl}octahydro-6H-pyrrolo[3,4-b]pyridin-6-yl]-1-cyclopropyl-6-fluoro-8-methoxy-4-oxo-1,4-dihydroquinoline-3-carboxylate |
| 52 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-[(4aS,7aS)-1-(tert-butoxycarbonyl)octahydro-6H-pyrrolo[3,4-b]pyridin-6-yl]-1-cyclopropyl-6-fluoro-8-methoxy-4-oxo-1,4-dihydroquinoline-3-carboxylate |
| 29 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-[(4aS,7aS)-octahydro-6H-pyrrolo[3,4-b]pyridin-6-yl]-4-oxo-1,4-dihydroquinoline-3-carboxylate |
| 30 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-{1-[(5-methyl-2-oxo-1,3-dioxol-4-yl)methyl]octahydro-6H-pyrrolo[3,4-b]pyridin-6-yl}-4-oxo-1,4-dihydroquinoline-3-carboxylate |
| 31 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-(1-{[(acetyloxy)methoxy]carbonyl}octahydro-6H-pyrrolo[3,4-b]pyridin-6-yl)-1-cyclopropyl-6-fluoro-8-methoxy-4-oxo-1,4-dihydroquinoline-3-carboxylate |
| 32 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-[(4aS,7aS)-octahydro-6H-pyrrolo[3,4-b]pyridin-6-yl]-4-oxo-1,4-dihydroquinoline-3-carboxylate |
| 33 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-{1-[(5-methyl-2-oxo-1,3-dioxol-4-yl)methyl]octahydro-6H-pyrrolo[3,4-b]pyridin-6-yl}-4-oxo-1,4-dihydroquinoline-3-carboxylate |
| 34 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-(1-{[(acetyloxy)methoxy]carbonyl}octahydro-6H-pyrrolo[3,4-b]pyridin-6-yl)-1-cyclopropyl-6-fluoro-8-methoxy-4-oxo-1,4-dihydroquinoline-3-carboxylate |
| 53 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-[(4aS,7aS)-1-(tert-butoxycarbonyl)octahydro-6H-pyrrolo[3,4-b]pyridin-6-yl]-1-cyclopropyl-6-fluoro-8-methoxy-4-oxo-1,4-dihydroquinoline-3-carboxylate |
| 35 | 2-[(8R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-1-cyclopropyl-6-fluoro-8-methoxy-7-[(4aS,7aS)-octahydro-6H-pyrrolo[3,4-b]pyridin-6-yl]-4-oxo-1,4-dihydroquinoline-3-carboxylate |

TABLE 2-continued

| Compound No. | IUPAC name |
|---|---|
| 36 | 2-[(8R,9R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-1-cyclopropyl-6-fluoro-8-methoxy-7-{1-[(5-methyl-2-oxo-1,3-dioxol-4-yl)methyl]octahydro-6H-pyrrolo[3,4-b]pyridin-6-yl}-4-oxo-1,4-dihydroquinoline-3-carboxylate |
| 37 | 2-[(8R,9R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-7-(1-{[(acetyloxy)methoxy]carbonyl}octahydro-6H-pyrrolo[3,4-b]pyridin-6-yl)-1-cyclopropyl-6-fluoro-8-methoxy-4-oxo-1,4-dihydroquinoline-3-carboxylate |
| 38 | 2-[(4aR,4bS,5R,6aR,6bR,9aS,10aR,10bR)-4b-fluoro-5-hydroxy-4a,6a,8,8-tetramethyl-2-oxo-2,4a,4b,5,6,6a,9a,10,10a,10b,11,12-dodecahydro-6bH-naphtho[2',1':4,5]indeno[1,2-d][1,3]dioxol-6b-yl]-2-oxoethyl rel-1-cyclopropyl-6-fluoro-8-methoxy-7-{1-[(5-methyl-2-oxo-1,3-dioxol-4-yl)methyl]octahydro-6H-pyrrolo[3,4-b]pyridin-6-yl}-4-oxo-1,4-dihydroquinoline-3-carboxylate |
| 39 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-[(3S)-3-aminoazepan-1-yl]-8-chloro-1-cyclopropyl-6-fluoro-4-oxo-1,4-dihydroquinoline-3-carboxylate |
| 40 | 2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-[(3S)-3-aminoazepan-1-yl]-8-chloro-1-cyclopropyl-6-fluoro-4-oxo-1,4-dihydroquinoline-3-carboxylate |
| 41 | 2-[(8R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-[(3S)-3-aminoazepan-1-yl]-8-chloro-1-cyclopropyl-6-fluoro-4-oxo-1,4-dihydroquinoline-3-carboxylate |
| 42 | 2-[(8R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-7-[(3S)-3-aminoazepan-1-yl]-8-chloro-1-cyclopropyl-6-fluoro-4-oxo-1,4-dihydroquinoline-3-carboxylate |
| 43 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-(3R)-9-fluoro-3-methyl-10-(4-methylpiperazin-1-yl)-7-oxo-2,3-dihydro-7H-[1,4]oxazino[2,3,4-ij]quinoline-6-carboxylate |
| 44 | 2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-(3R)-9-fluoro-3-methyl-10-(4-methylpiperazin-1-yl)-7-oxo-2,3-dihydro-7H-[1,4]oxazino[2,3,4-ij]quinoline-6-carboxylate |
| 45 | 2-[(8R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-(3R)-9-fluoro-3-methyl-10-(4-methylpiperazin-1-yl)-7-oxo-2,3-dihydro-7H-[1,4]oxazino[2,3,4-ij]quinoline-6-carboxylate |
| 46 | 2-[(8R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-(3R)-9-fluoro-3-methyl-10-(4-methylpiperazin-1-yl)-7-oxo-2,3-dihydro-7H-[1,4]oxazino[2,3,4-ij]quinoline-6-carboxylate |

In another embodiment, the compounds disclosed herein comprise gatifloxacin and betamethasone, such as:

2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate;

2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-{3-methyl-4-[(5-methyl-2-oxo-1,3-dioxol-4-yl)methyl]piperazin-1-yl}-4-oxo-1,4-dihydroquinoline-3-carboxylate;

2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-(4-{[(acetyloxy)methoxy]carbonyl}-3-methylpiperazin-1-yl)-1-cyclopropyl-6-fluoro-8-methoxy-4-oxo-1,4-dihydroquinoline-3-carboxylate;

2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-(4-{[1-(acetyloxy)ethoxy]carbonyl}-3-methylpiperazin-1-yl)-1-cyclopropyl-6-fluoro-8-methoxy-4-oxo-1,4-dihydroquinoline-3-carboxylate;

2-[(8R,9S,10R,11R,13R,14R,16R,17S)-17-(acetyloxy)-9-fluoro-11-hydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate;

2-[(8R,9S,10R,11R,13R,14R,16R,17S)-17-(butanoyloxy)-9-fluoro-11-hydroxy-10,13,16-trimethyl-3-oxo-6,7,8,9,10,11,12,13,14,15,16,17-dodecahydro-3H-cyclopenta[a]

phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate;

2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-[4-(tert-butoxycarbonyl)-3-methylpiperazin-1-yl]-1-cyclopropyl-6-fluoro-8-methoxy-4-oxo-1,4-dihydroquinoline-3-carboxylate.

In another embodiment, the compounds disclosed herein comprise gatifloxacin and dexamethasone, such as:

2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate;

2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-{3-methyl-4-[(5-methyl-2-oxo-1,3-dioxol-4-yl)methyl]piperazin-1-yl}-4-oxo-1,4-dihydroquinoline-3-carboxylate;

2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-(4-{[1-(acetyloxy)ethoxy]carbonyl}-3-methylpiperazin-1-yl)-1-cyclopropyl-6-fluoro-8-methoxy-4-oxo-1,4-dihydroquinoline-3-carboxylate;

2-[(8R,9S,10R,11R,13R,14R,16S,17S)-17-(butanoyloxy)-9-fluoro-11-hydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate;

2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methyl-4-{[(5-methyl-2-oxo-1,3-dioxol-4-yl)methoxy]carbonyl}piperazin-1-yl)-4-oxo-1,4-dihydroquinoline-3-carboxylate;

2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-[4-(tert-butoxycarbonyl)-3-methylpiperazin-1-yl]-1-cyclopropyl-6-fluoro-8-methoxy-4-oxo-1,4-dihydroquinoline-3-carboxylate.

In another embodiment, the compounds disclosed herein comprise gatifloxacin and prednisolone, such as:

2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate;

2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-{3-methyl-4-[(5-methyl-2-oxo-1,3-dioxol-4-yl)methyl]piperazin-1-yl}-4-oxo-1,4-dihydroquinoline-3-carboxylate;

2-[(8R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-(4-{[(acetyloxy)methoxy]carbonyl}-3-methylpiperazin-1-yl)-1-cyclopropyl-6-fluoro-8-methoxy-4-oxo-1,4-dihydroquinoline-3-carboxylate;

2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-(4-{[1-(acetyloxy)ethoxy]carbonyl}-3-methylpiperazin-1-yl)-1-cyclopropyl-6-fluoro-8-methoxy-4-oxo-1,4-dihydroquinoline-3-carboxylate;

2-[(8R,10S,11R,13R,14R,17S)-17-(butanoyloxy)-11-hydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate;

2-{(8R,10S,11R,13R,14R,17S)-11-hydroxy-10,13-dimethyl-3-oxo-17-[(phenylcarbonyl)oxy]-6,7,8,9,10,11,12,13,14,15,16,17-dodecahydro-3H-cyclopenta[a]phenanthren-17-yl}-2-oxoethyl rel-1-cyclopropyl-6-fluoro-8-methoxy-7-(3-methylpiperazin-1-yl)-4-oxo-1,4-dihydroquinoline-3-carboxylate;

2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methyl-4-{[(5-methyl-2-oxo-1,3-dioxol-4-yl)methoxy]carbonyl}piperazin-1-yl)-4-oxo-1,4-dihydroquinoline-3-carboxylate;

2-[(10R,11S,13S,17R)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-[4-(2-amino-3-methylbutanoyl)-3-methylpiperazin-1-yl]-1-cyclopropyl-6-fluoro-8-methoxy-4-oxo-1,4-dihydroquinoline-3-carboxylate;

rel-(2R)-2-amino-4-{4-[1-cyclopropyl-3-({2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethoxy}carbonyl)-6-fluoro-8-methoxy-4-oxo-1,4-dihydroquinolin-7-yl]-2-methylpiperazin-1-yl}-4-oxobutanoic acid;

2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-(4-{2-[(2-amino-3-methyl butanoyl)amino]-3-methylbutanoyl}-3-methylpiperazin-1-yl)-1-cyclopropyl-6-fluoro-8-methoxy-4-oxo-1,4-dihydroquinoline-3-carboxylate;

rel-2-amino-5-{[({4-[1-cyclopropyl-3-({2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethoxy}carbonyl)-6-fluoro-8-methoxy-4-oxo-1,4-dihydroquinolin-7-yl]-2-methylpiperazin-1-yl}carbonyl)oxy]methoxy}-5-oxopentanoic acid;

2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-(4-{[({2-[(2-amino-3-methylbutanoyl)amino]-3-methylbutanoyl}oxy)methoxy]carbonyl}-3-methylpiperazin-1-yl)-1-cyclopropyl-6-fluoro-8-methoxy-4-oxo-1,4-dihydroquinoline-3-carboxylate;

2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-[4-(tert-butoxycarbonyl)-3-methylpiperazin-1-yl]-1-cyclopropyl-6-fluoro-8-methoxy-4-oxo-1,4-dihydroquinoline-3-carboxylate.

In another embodiment, the compounds disclosed herein comprise gatifloxacin and hydrocortisone, such as:

2-[(8R,9R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-7-[4-(tert-butoxycarbonyl)-3-methylpiperazin-1-yl]-1-cyclopropyl-6-fluoro-8-methoxy-4-oxo-1,4-dihydroquinoline-3-carboxylate;

2-[(8R,9R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate;

2-[(8R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-1-cyclopropyl-6-fluoro-8-methoxy-7-{3-methyl-4-[(5-methyl-2-oxo-1,3-dioxol-4-yl)methyl]piperazin-1-yl}-4-oxo-1,4-dihydroquinoline-3-carboxylate;

2-[(10R,11S,13S,17R)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-7-(4-{[1-(acetyloxy)ethoxy]carbonyl}-3-methylpiperazin-1-yl)-1-cyclopropyl-6-fluoro-8-methoxy-4-oxo-1,4-dihydroquinoline-3-carboxylate;

2-{(8R,10S,11R,13R,14R,17S)-11-hydroxy-10,13-dimethyl-3-oxo-17-[(phenylcarbonyl)oxy]-2,3,6,7,8,9,10,11,12,13,14,15,16,17-tetradecahydro-1H-cyclopenta[a]phenanthren-17-yl}-2-oxoethyl rel-1-cyclopropyl-6-fluoro-8-methoxy-7-(3-methylpiperazin-1-yl)-4-oxo-1,4-dihydroquinoline-3-carboxylate;

2-{(8R,9R,10S,11R,13R,14R,17S)-11-hydroxy-10,13-dimethyl-3-oxo-17-[(phenylcarbonyl)oxy]-2,3,6,7,8,9,10,11,12,13,14,15,16,17-tetradecahydro-1H-cyclopenta[a]phenanthren-17-yl}-2-oxoethyl rel-7-(4-{[1-(acetyloxy)ethoxy]carbonyl}-3-methylpiperazin-1-yl)-1-cyclopropyl-6-fluoro-8-methoxy-4-oxo-1,4-dihydroquinoline-3-carboxylate.

In another embodiment, the compounds disclosed herein comprise gatifloxacin and triamcinolone acetonide, such as:

2-[(4aR,4bS,5R,6aR,6bR,9aS,10aR,10bR)-4b-fluoro-5-hydroxy-4a,6a,8,8-tetramethyl-2-oxo-2,4a,4b,5,6,6a,9a,10,10a,10b,11,12-dodecahydro-6bH-naphtho[2',1':4,5]indeno[1,2-d][1,3]dioxol-6b-yl]-2-oxoethyl rel-7-(4-{[1-(acetyloxy)ethoxy]carbonyl}-3-methylpiperazin-1-yl)-1-cyclopropyl-6-fluoro-8-methoxy-4-oxo-1,4-dihydroquinoline-3-carboxylate;

2-[(4aR,4bS,5R,6aR,6bR,9aS,10aR,10bR)-4b-fluoro-5-hydroxy-4a,6a,8,8-tetramethyl-2-oxo-2,4a,4b,5,6,6a,9a,10,10a,10b,11,12-dodecahydro-6bH-naphtho[2',1':4,5]indeno[1,2-d][1,3]dioxol-6b-yl]-2-oxoethyl rel-1-cyclopropyl-6-fluoro-8-methoxy-7-{3-methyl-4-[(5-methyl-2-oxo-1,3-dioxol-4-yl)methyl]piperazin-1-yl}-4-oxo-1,4-dihydroquinoline-3-carboxylate.

In another embodiment, the compounds disclosed herein comprise moxifloxacin and betamethasone, such as:

2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-[(4aS,7aS)-octahydro-6H-pyrrolo[3,4-b]pyridin-6-yl]-4-oxo-1,4-dihydroquinoline-3-carboxylate;

2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-{1-[(5-methyl-2-oxo-1,3-dioxol-4-yl)methyl]octahydro-6H-pyrrolo[3,4-b]pyridin-6-yl}-4-oxo-1,4-dihydroquinoline-3-carboxylate;

2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-[(4aS,7aS)-1-{[(acetyloxy)methoxy]carbonyl}octahydro-6H-pyrrolo[3,4-b]pyridin-6-yl]-1-cyclopropyl-6-fluoro-8-methoxy-4-oxo-1,4-dihydroquinoline-3-carboxylate;

2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-[(4aS,7aS)-1-(tert-butoxycarbonyl)octahydro-6H-pyrrolo[3,4-b]pyridin-6-yl]-1-cyclopropyl-6-fluoro-8-methoxy-4-oxo-1,4-dihydroquinoline-3-carboxylate.

In another embodiment, the compounds disclosed herein comprise Moxifloxacin and dexamethasone, such as:

2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-[(4aS,7aS)-octahydro-6H-pyrrolo[3,4-b]pyridin-6-yl]-4-oxo-1,4-dihydroquinoline-3-carboxylate;

2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-{1-[(5-methyl-2-oxo-1,3-dioxol-4-yl)methyl]octahydro-6H-pyrrolo[3,4-b]pyridin-6-yl}-4-oxo-1,4-dihydroquinoline-3-carboxylate;

2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-(1-{[(acetyloxy)methoxy]carbonyl}octahydro-6H-pyrrolo[3,4-b]pyridin-6-yl)-1-cyclopropyl-6-fluoro-8-methoxy-4-oxo-1,4-dihydroquinoline-3-carboxylate;

In another embodiment, the compounds disclosed herein comprise moxifloxacin and prednisolone, such as:

2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-[(4aS,7aS)-octahydro-6H-pyrrolo[3,4-b]pyridin-6-yl]-4-oxo-1,4-dihydroquinoline-3-carboxylate;

2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-{1-[(5-methyl-2-oxo-1,3-dioxol-4-yl)methyl]octahydro-6H-pyrrolo[3,4-b]pyridin-6-yl}-4-oxo-1,4-dihydroquinoline-3-carboxylate;

2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-(1-{[(acetyloxy)methoxy]carbonyl}octahydro-6H-pyrrolo[3,4-b]pyridin-6-yl)-1-cyclopropyl-6-fluoro-8-methoxy-4-oxo-1,4-dihydroquinoline-3-carboxylate;

2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-[(4aS,7aS)-1-(tert-butoxycarbonyl)octahydro-6H-pyrrolo[3,4-b]pyridin-6-yl]-1-cyclopropyl-6-fluoro-8-methoxy-4-oxo-1,4-dihydroquinoline-3-carboxylate.

In another embodiment, the compounds disclosed herein comprise moxifloxacin and hydrocortisone, such as:

2-[(8R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-1-cyclopropyl-6-fluoro-8-methoxy-7-[(4aS,7aS)-octahydro-6H-pyrrolo[3,4-b]pyridin-6-yl]-4-oxo-1,4-dihydroquinoline-3-carboxylate;

2-[(8R,9R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-1-cyclopropyl-6-fluoro-8-methoxy-7-{1-[(5-methyl-2-oxo-1,3-dioxol-4-yl)methyl]octahydro-6H-pyrrolo[3,4-b]pyridin-6-yl}-4-oxo-1,4-dihydroquinoline-3-carboxylate;

2-[(8R,9R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-7-(1-{[(acetyloxy)methoxy]carbonyl}octahydro-6H-pyrrolo[3,4-b]pyridin-6-yl)-1-cyclopropyl-6-fluoro-8-methoxy-4-oxo-1,4-dihydroquinoline-3-carboxylate.

In another embodiment, the compounds disclosed herein comprise moxifloxacin and triamcinolone acetonide, such as:

2-[(4aR,4bS,5R,6aR,6bR,9aS,10aR,10bR)-4b-fluoro-5-hydroxy-4a,6a,8,8-tetramethyl-2-oxo-2,4a,4b,5,6,6a,9a,10,10a,10b,11,12-dodecahydro-6bH-naphtho[2',1':4,5]indeno[1,2-d][1,3]dioxol-6b-yl]-2-oxoethyl rel-1-cyclopropyl-6-fluoro-8-methoxy-7-{1-[(5-methyl-2-oxo-1,3-dioxol-4-yl)methyl]octahydro-6H-pyrrolo[3,4-b]pyridin-6-yl}-4-oxo-1,4-dihydroquinoline-3-carboxylate.

In another embodiment, the compounds disclosed herein comprise Besifloxacin and betamethasone, such as:

2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-[(3S)-3-aminoazepan-1-yl]-8-chloro-1-cyclopropyl-6-fluoro-4-oxo-1,4-dihydroquinoline-3-carboxylate.

In another embodiment, the compounds disclosed herein comprise Besifloxacin and dexamethasone, such as:

2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-7-[(3S)-3-aminoazepan-1-yl]-8-chloro-1-cyclopropyl-6-fluoro-4-oxo-1,4-dihydroquinoline-3-carboxylate.

In another embodiment, the compounds disclosed herein comprise besifloxacin and prednisolone, such as:

2-[(8R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-[(3S)-3-aminoazepan-1-yl]-8-chloro-1-cyclopropyl-6-fluoro-4-oxo-1,4-dihydroquinoline-3-carboxylate.

In another embodiment, the compounds disclosed herein comprise besifloxacin and hydrocortisone, such as:

2-[(8R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-7-[(3S)-3-aminoazepan-1-yl]-8-chloro-1-cyclopropyl-6-fluoro-4-oxo-1,4-dihydroquinoline-3-carboxylate.

In another embodiment, the compounds disclosed herein comprise besifloxacin and levofloxacin, such as:

2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-(3R)-9-fluoro-3-methyl-10-(4-methyl piperazin-1-yl)-7-oxo-2,3-dihydro-7H-[1,4]oxazino[2,3,4-ij]quinoline-6-carboxylate.

In another embodiment, the compounds disclosed herein comprise dexamethasone and levofloxacin, such as:

2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-(3R)-9-fluoro-3-methyl-10-(4-methyl piperazin-1-yl)-7-oxo-2,3-dihydro-7H-[1,4]oxazino[2,3,4-ij]quinoline-6-carboxylate.

In another embodiment, the compounds disclosed herein comprise prednisolone and levofloxacin, such as:

2-[(8R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-(3R)-9-fluoro-3-methyl-10-(4-methylpiperazin-1-yl)-7-oxo-2,3-dihydro-7H-[1,4]oxazino[2,3,4-ij]quinoline-6-carboxylate.

In another embodiment, the compounds disclosed herein comprise Hydrocortisone and levofloxacin, such as:

2-[(8R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-(3R)-9-fluoro-3-methyl-10-(4-methylpiperazin-1-yl)-7-oxo-2,3-dihydro-7H-[1,4]oxazino[2,3,4-ij]quinoline-6-carboxylate.

Some compounds of the invention have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of the invention are able to form.

The acid addition salt form of a compound of the invention that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic acid and the like (Handbook of Pharmaceutical Salts, P. Heinrich Stahl & Camille G. Wermuth (Eds), Verlag Helvetica Chimica Acta-Zürich, 2002, 329-345).

The base addition salt form of a compound of the invention that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahl & Camille G. Wermuth (Eds), Verlag Helvetica Chimica Acta-Zürich, 2002, 329-345).

Compounds of the invention and their salts can be in the form of a solvate, which is included within the scope of the present invention. Such solvates include for example hydrates, alcoholates and the like.

In still another embodiment of the invention, there are provided methods for treating or preventing eye conditions such as: conjunctivitis, keratitis, endophthalmitis, blepharitis, dacryocystitis, hordeolum, corneal ulcers, anterior blepharitis, posterior blepharitis, meibomian gland dysfunction, dry eye disease (keratoconjunctivitis sicca) ocular pain, ocular pain and inflammation post-ocular surgery, bacterial conjunctivitis, anterior uveitis, in a patient suffering thereof. Such methods can be performed, for example, by administering to a subject in need thereof a therapeutically effective amount of at least one compound of the invention, or any combination thereof, or pharmaceutically acceptable salts, hydrates, solvates, crystal forms thereof.

The present invention concerns the use of a compound of the invention or a pharmaceutically acceptable salt thereof, for the manufacture of a medicament for the treatment of conjunctivitis, keratitis, blepharitis, dacryocystitis, hordeolum, corneal ulcers, anterior blepharitis, posterior blepharitis, meibomian gland dysfunction, dry eye disease (keratoconjunctivitis sicca) ocular pain, ocular pain and inflammation post-ocular surgery, bacterial conjunctivitis, anterior uveitis.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The compounds of the invention may also be administered as pharmaceutical compositions in a form suitable for topical use, for example, as oily suspensions, as solutions or suspensions in aqueous liquids or nonaqueous liquids, or as oil-in-water or water-in-oil liquid emulsions.

Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate.

A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.8 |
| antioxidant | as needed |
| surfactant | as needed |
| purified water | to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 µl.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions such as conjunctivitis, keratitis, endophthalmitis, blepharitis, dacryocystitis, hordeolum, corneal ulcers, anterior blepharitis, posterior blepharitis, meibomian gland dysfunction, dry eye disease (keratoconjunctivitis sicca) ocular pain, ocular pain and inflammation post-ocular surgery, bacterial conjunctivitis, anterior uveitis, post-surgical inflammation, inflammatory conditions of the palpebral and bulbar conjunctiva, cornea, and anterior segment of the globe, such as allergic conjunctivitis, ocular rosacea, dry eye, blepharitis, meibomian gland dysfunction, superficial punctate keratitis, herpes zoster keratitis, iritis, cyclitis, selected infective conjunctivitis, corneal injury from chemical radiation, or thermal burns, penetration of foreign bodies, allergy, and combinations thereof.

Thus, in further embodiments of the invention, there are provided methods for treating conjunctivitis, keratitis, blepharitis, endophthalmitis, dacryocystitis, hordeolum, corneal ulcers, anterior blepharitis, posterior blepharitis, meibomian gland dysfunction, dry eye disease (keratoconjunctivitis sicca) ocular pain, ocular pain and inflammation post-ocular surgery, bacterial conjunctivitis, anterior uveitis, post-surgical inflammation, inflammatory conditions of the palpebral and bulbar conjunctiva, cornea, and anterior segment of the globe, such as allergic conjunctivitis, ocular rosacea, dry eye, blepharitis, meibomian gland dysfunction, superficial punctate keratitis, herpes zoster keratitis, iritis, cyclitis, selected infective conjunctivitis, corneal injury from chemical radiation, or thermal burns, penetration of foreign bodies, allergy, and combinations thereof Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of the invention. The compounds according to the invention can be prepared analogously to conventional methods as understood by the person skilled in the art of synthetic organic chemistry. Schemes 1, 2, 3 and 4 set forth below, illustrate how the compounds according to the invention can be made. It should be noted that the brief description on each of the arrows for each conversion has been added for illustration purpose sonly and should not be regarded as limiting with respect to the sequence of each individual step.
The following abbreviations are used in the general schemes and in the examples:
Boc tert-Butyloxycarbonyl
EDCI 1-Ethyl-3-(3-dimethylaminopropyl)carbodiimide
Boc$_2$O di-tert-butyl dicarbonate
THF tetrahydrofuran
NaOH sodium hydroxide
DMAP 4-dimethylaminopyridine
CH$_2$Cl$_2$ dichloromethane
HCl hydrochloric acid
M molar
NaHCO$_3$ sodium bicarbonate
CHCl3 chloroform
EtOH ethanol
DMF N,N-dimethylformamide
MeOH methanol
NaOAc sodium acetate
FA fumaric acid SCHEME 1
In this scheme the synthesis of hybrid analogs was started with gatifloxacin. Boc protection gave the Boc-gatifloxacin. EDCI coupling with appropriate prednisolone, followed by removal of the BOC group and fumaric acid treatment yielded the desired antibiotic/steroid Compound 12.

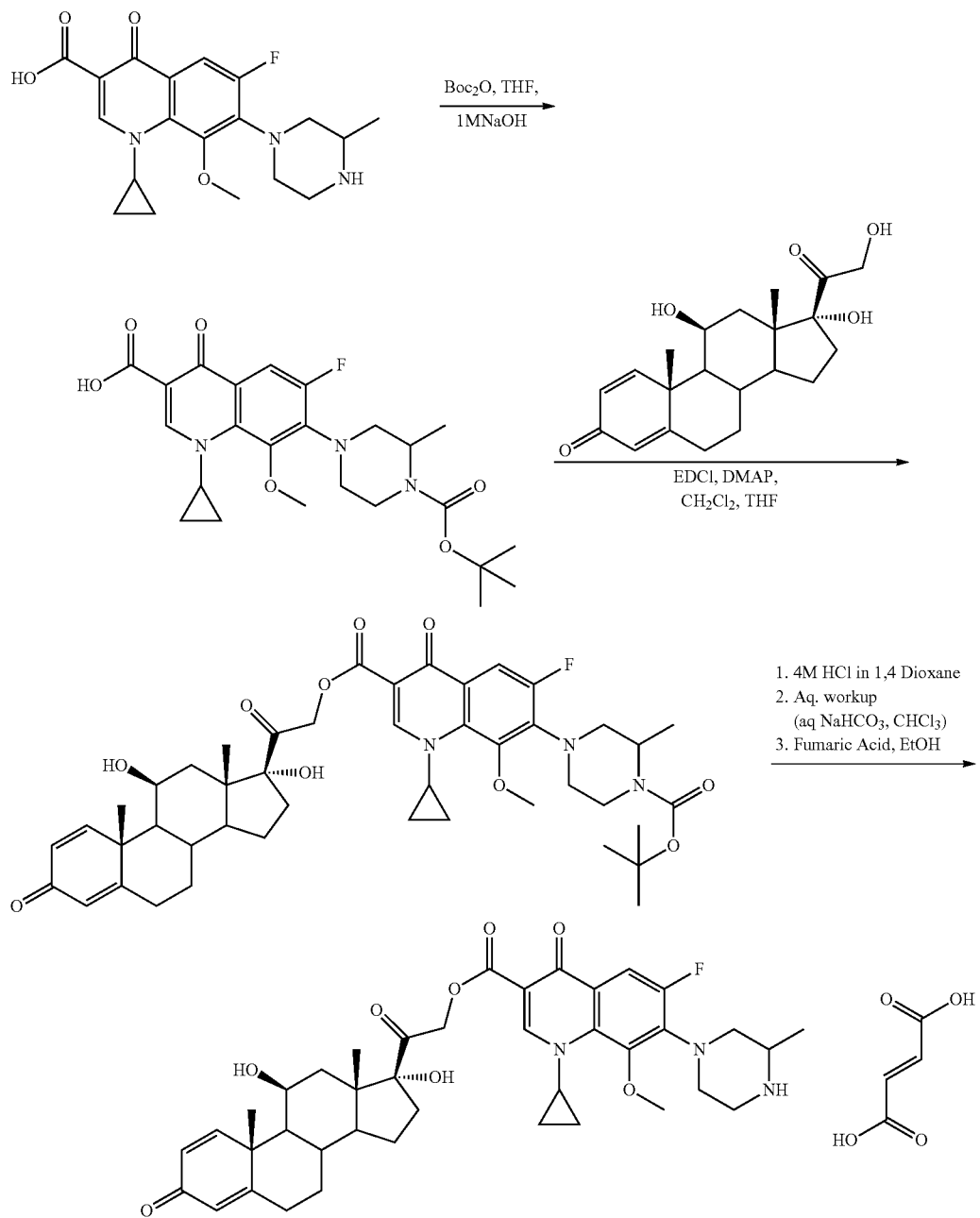

SCHEME 2

In this scheme the synthesis of hybrid analogs was started with gatifloxacin. Gatifloxacin was reacted with a pro-drug precursor. EDCl coupling with prednisolone, and purification using MeOH and $CH_2Cl_2$ yielded the desired antibiotic/steroid Compound 13.

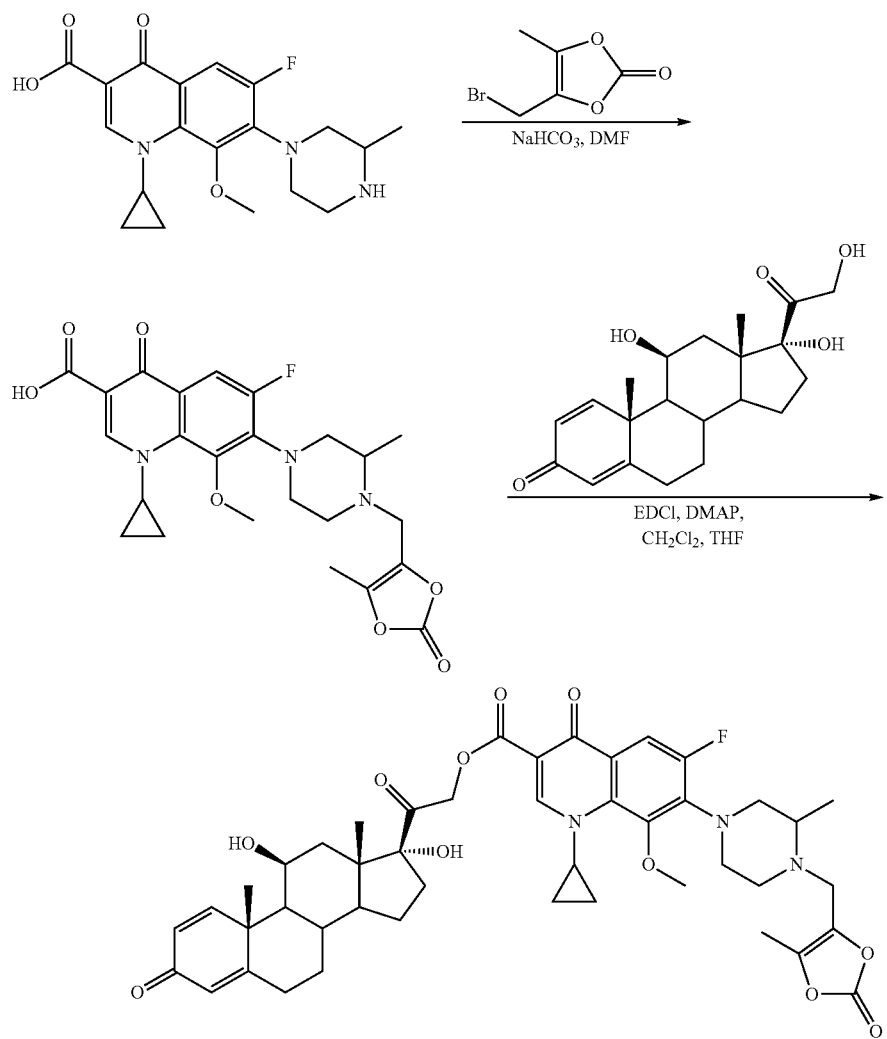

SCHEME 3

In this scheme the synthesis of hybrid analogs was started with gatifloxacin. Gatifloxacin was reacted with a pro-drug precursor followed by NaOAc treatment. EDCl coupling with prednisolone, and purification using MeOH and $CH_2Cl_2$ yielded the desired antibiotics/steriod compound 14.

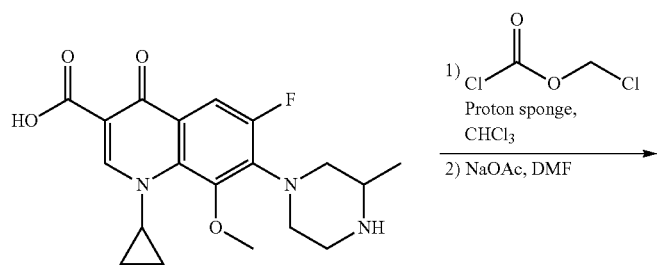

-continued

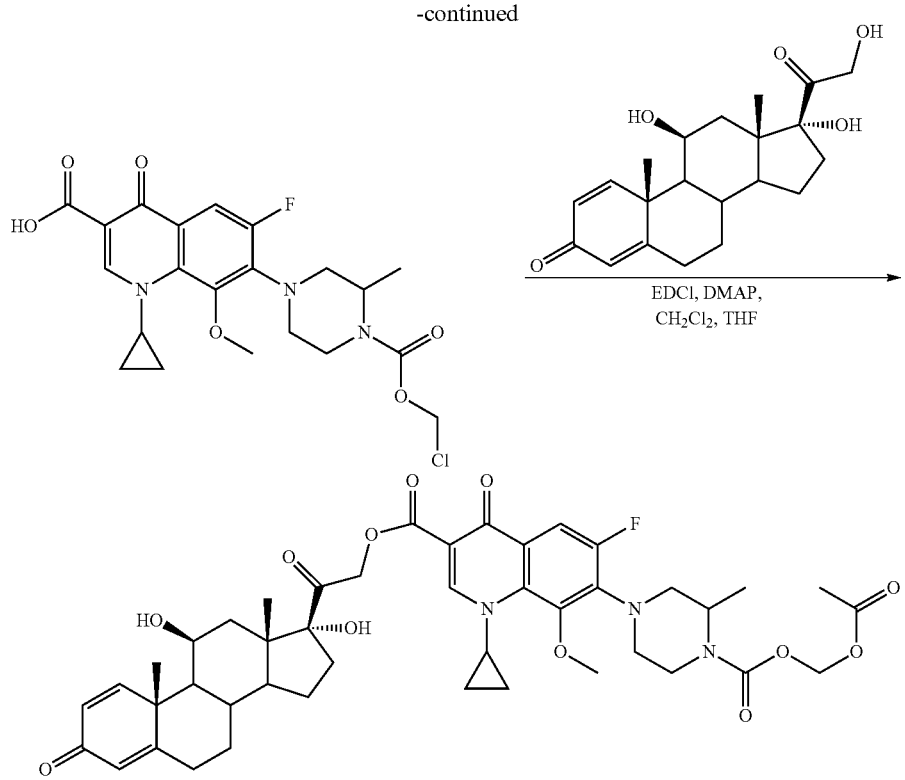

SCHEME 4
In this scheme the synthesis of hybrid analogs was started levofloxacin. EDCl coupling with prednisolone, and purification using MeOH and CH$_2$Cl$_2$ yielded the compound 45.

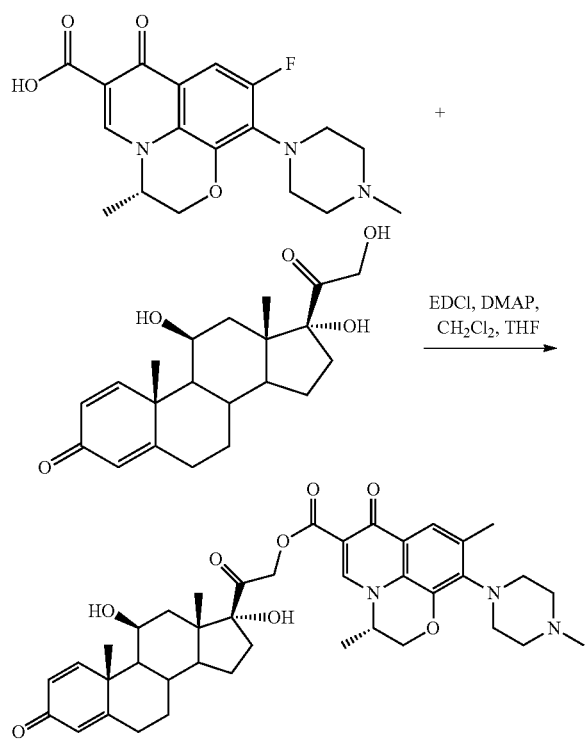

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of hydrogen $^1$H (or H) or use of $^{13}$C enriched material in place of $^{12}$O and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

Compound names were generated with ACDLabs version 12.5 or ChemBioDraw Ultra version 12.0.2.

In general, characterization of the compounds is performed according to the following methods. Proton nuclear magnetic resonance ($^1$H NMR) and carbon nuclear magnetic resonance ($^{13}$C NMR) spectra were recorded on a Varian 300 or 600 MHz spectrometer in deuterated solvent. Chemical shifts were reported as δ (delta) values in parts per million (ppm) relative to tetramethylsilane (TMS) as an internal standard (0.00 ppm) and multiplicities were reported as s, singlet; d, doublet; t, triplet; q, quartet; m, multiplet; br, broad. Data were reported in the following format: chemical shift (multiplicity, coupling constant(s) J in hertz (Hz), integrated intensity). The mass spectrometry data were determined on a Shimadzu LCMS-IT-TOF instrument.

The formation of the hybrid compounds was checked by $^1$H-NMR by comparing the chemical shifts of protons H$^a$, H$^b$ from the antibiotic molecule and of protons H$^c$ and/or H$^d$ of the steroid molecule with the chemical shifts of these same protons on the newly formed hybrid molecule noted H$^{a*}$, H$^{b*}$, H$^{c*}$ and/or H$^{d*}$ wherein "*" indicates the hybrid compound. Applicants have indicated with arrows the location of these protons and the reaction site of the pro-drug moiety, where available. Each scheme shows the formation of the new hybrid drug. Each table describes the results for the new hybrid drug and the pro-drug number, where existing. The pro-drug moiety numbers are as described in Table 1.

The majority of the compounds of the invention were obtained by linking the antibiotic directly to the steroid. Each scheme shown below, represents the two drug entities which are linked together to form the new hybrid drug compound. Each table describes the results for the new hybrid drug. Gatifloxacin reacted with betamethasone to form the following hybrid compounds as shown in Scheme 5 with the results described in Table 3.

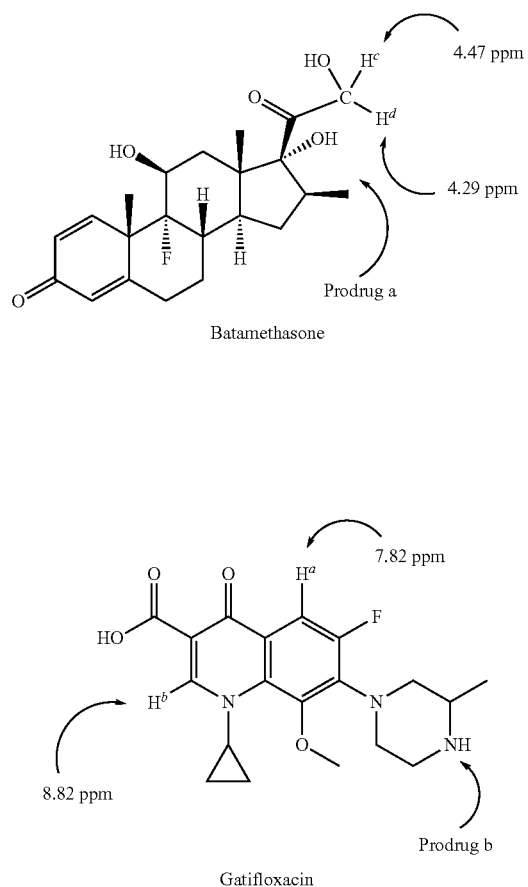

Scheme 5

Batamethasone

Gatifloxacin

TABLE 3

| * Comp No. Salt Pro-drug a Pro-drug b | Structure | δ ppm | | | | MASS |
|---|---|---|---|---|---|---|
| | | H$^{a*}$ | H$^{b*}$ | H$^{c*}$ | H$^{d*}$ | |
| 1 fumaric | 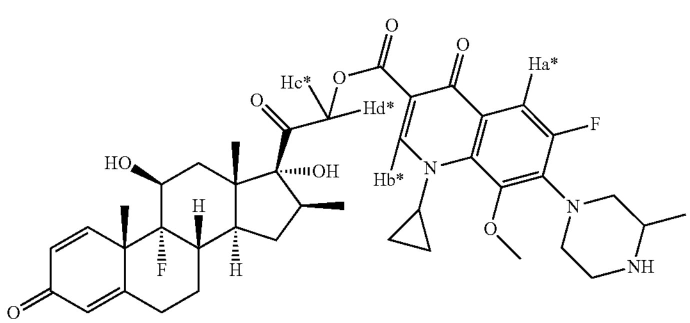 | 7.86 | 8.86 | 5.17 | 5.08 | 751 MNa$^+$ |

TABLE 3-continued

| * Comp No. Salt Pro-drug a Pro-drug b | Structure | δ ppm | | | | MASS |
|---|---|---|---|---|---|---|
| | | H$^{a*}$ | H$^{b*}$ | H$^{c*}$ | H$^{d*}$ | |
| 2 P$_b$3 | 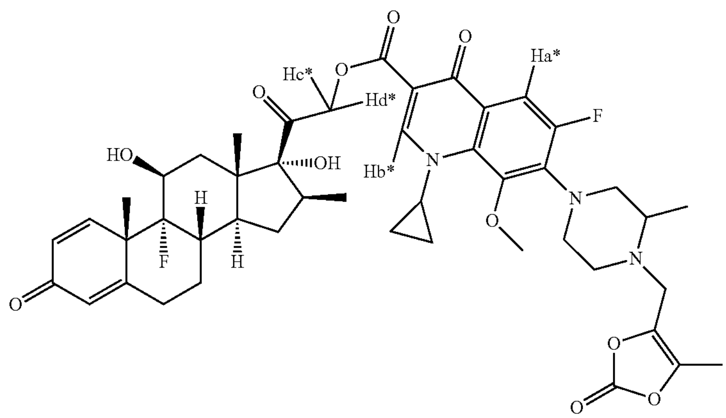 | 7.77 | 8.82 | 5.14 | 5.04 | |
| 3 P$_b$1 | 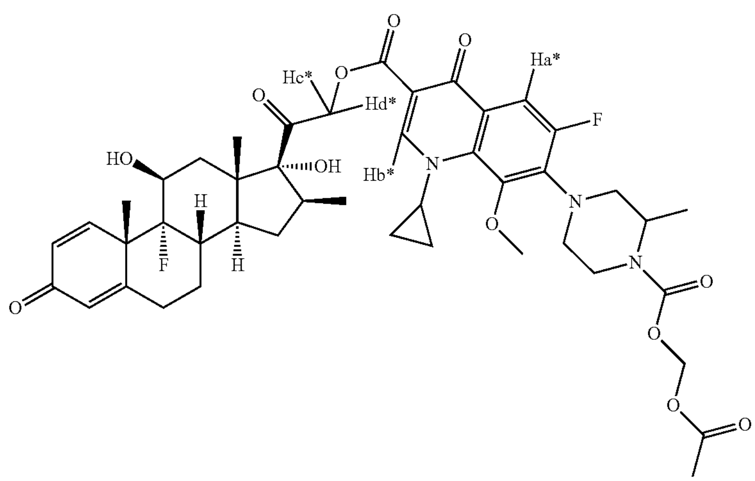 | 7.81 | 8.84 | 5.17 | 5.06 | 889 MNa$^+$ |
| 4 P$_b$2 | 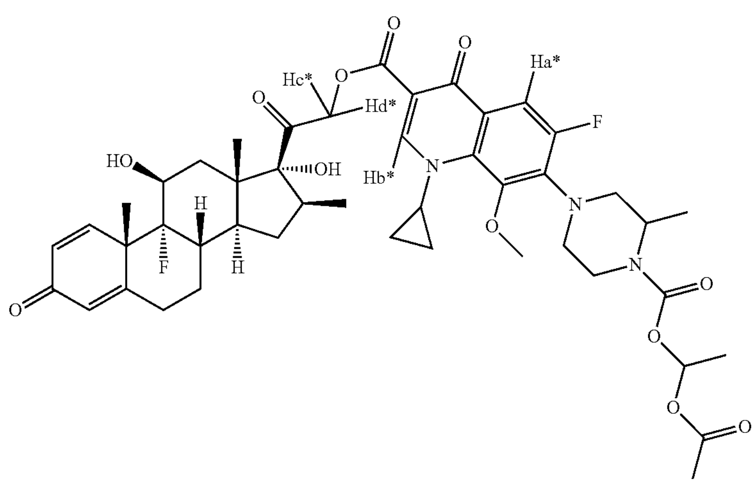 | 7.81 | 8.84 | 5.17 | 5.06 | |

TABLE 3-continued
| *Comp No. Salt Pro-drug a Pro-drug b | Structure | δ ppm H$^{a*}$ | H$^{b*}$ | H$^{c*}$ | H$^{d*}$ | MASS |
|---|---|---|---|---|---|---|
| 5 P$_a$11 | 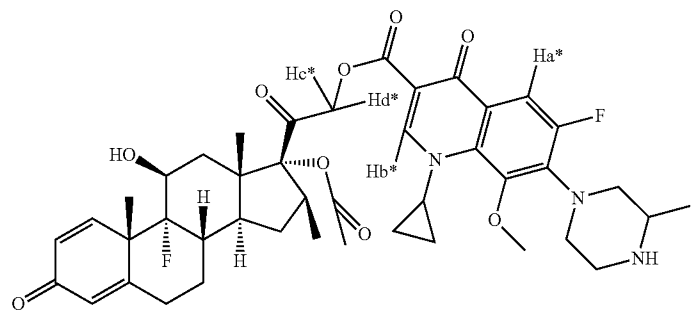 | 7.85 | 8.88 | 5.11 | 4.59 | 853 MNa$^+$ |
| 6 fumaric P$_a$12 | 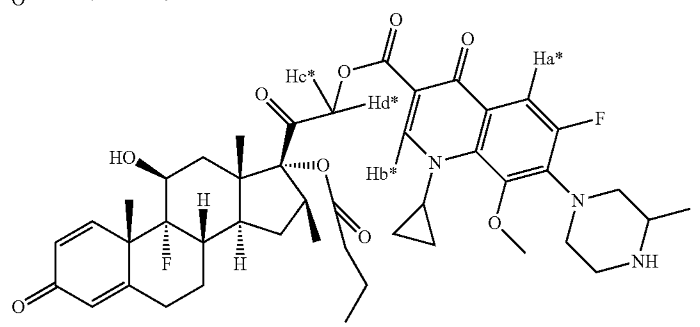 | 7.83 | 8.88 | 5.07 | 4.56 | 818 MH$^-$ |
| 57 P$_b$5 | 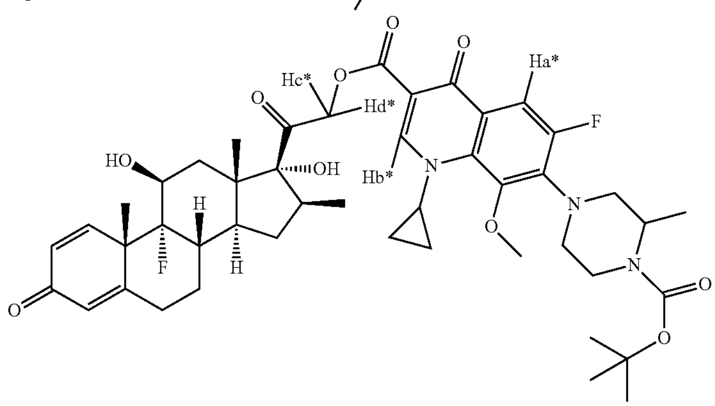 | 7.78 | 8.83 | 5.16 | 5.06 | 850 MH$^+$ |
Gatifloxacin reacted with dexamethasone to form the following hybrid compounds as shown in Scheme 6 with the results shown in Table 4.
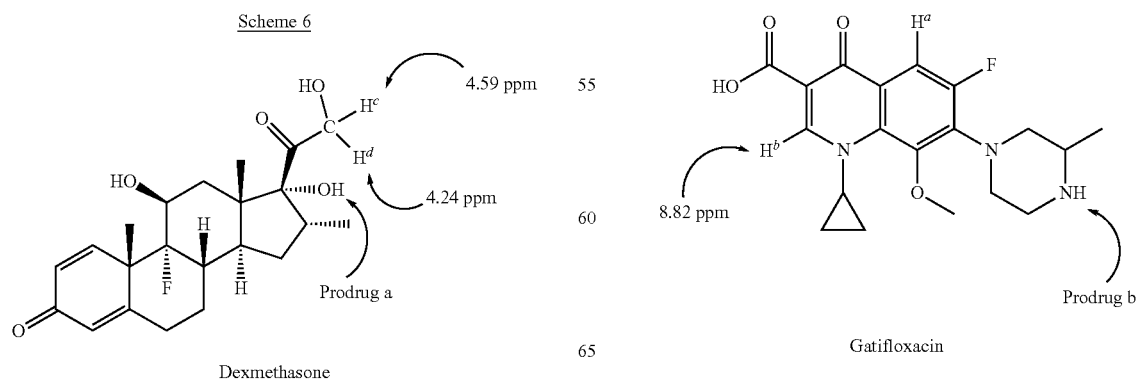
Scheme 6

TABLE 4

| * Comp No. Salt Pro-drug a Pro-drug b | Structure | δ ppm | | | | MASS |
|---|---|---|---|---|---|---|
| | | H$^{a}$* | H$^{b}$* | H$^{c}$* | H$^{d}$* | |
| 7 fumaric | 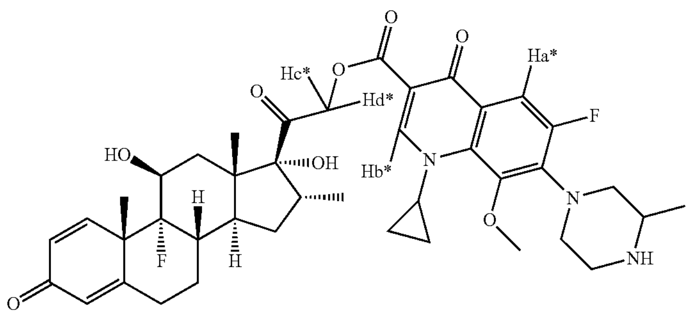 | 7.78 | 8.83 | 5.17 | 5.09 | 748 MH$^{-}$ |
| 8 P$_b$3 | 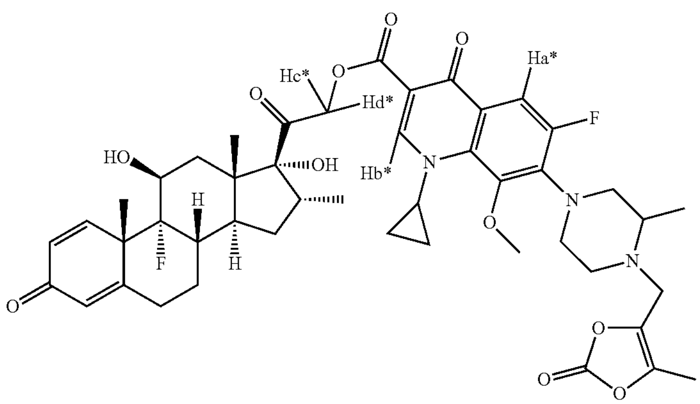 | 7.78 | 8.83 | 5.13 | | 884 MNa$^{+}$ |
| 9 P$_b$2 | 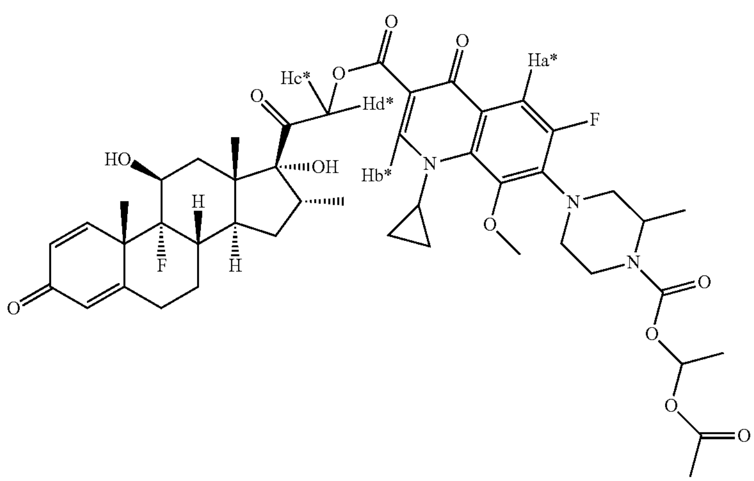 | 7.80 | 8.84 | 5.13 | | 903 MNa$^{+}$ |
| 10 Fumaric P$_a$12 | 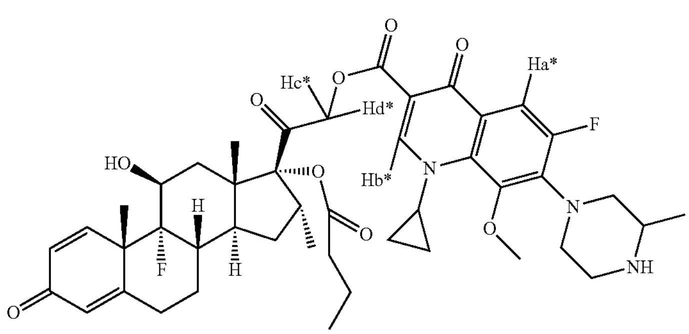 | 7.82 | 8.87 | 5.05 | | 818 MH$^{-}$ |

TABLE 4-continued
| * Comp No. Salt Pro-drug a Pro-drug b | Structure | δ ppm | | | | MASS |
|---|---|---|---|---|---|---|
| | | $H^{a*}$ | $H^{b*}$ | $H^{c*}$ | $H^{d*}$ | |
| 11 $P_b4$ | 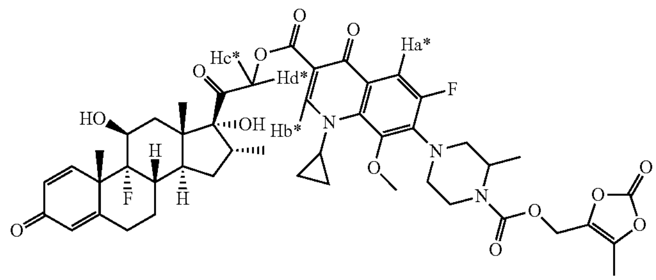 | 7.79 | 8.83 | 5.13 | | 906 $MH^+$ |
| 56 $P_b5$ | 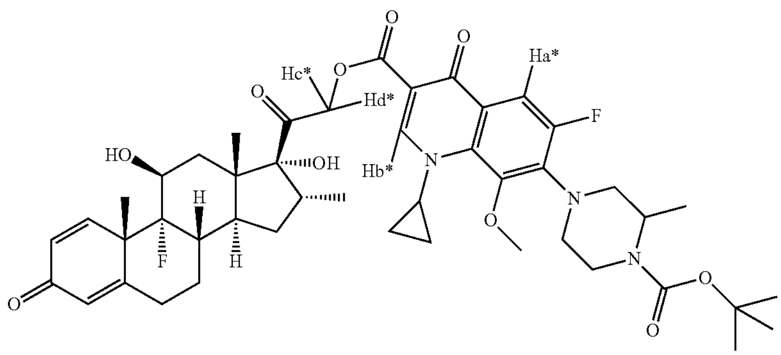 | 7.78 | 8.82 | 5.15 | 5.09 | |
Gatifloxacin reacted with prednisolone to form the following hybrid compounds as shown in Scheme 7 with the results shown in Table 5.
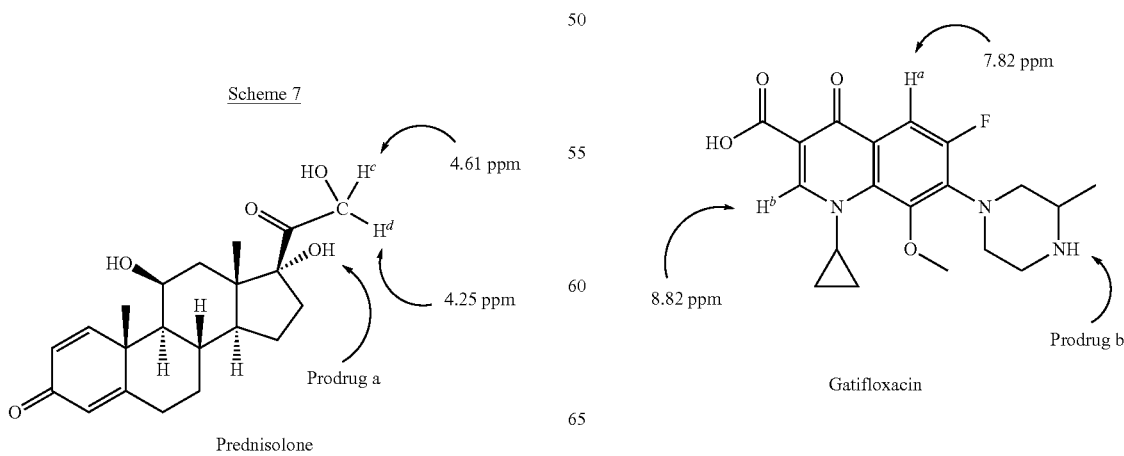
Scheme 7
Prednisolone
Prodrug a
Gatifloxacin
Prodrug b

TABLE 5

| Comp No. Pro-drug a Pro-drug b Salt | Structure | δ ppm | | | | MASS |
|---|---|---|---|---|---|---|
| | | H$^{a*}$ | H$^{b*}$ | H$^{c*}$ | H$^{d*}$ | |
| 12 fumaric | | 7.84 | 8.85 | 5.16 | | 716 MH$^-$ |
| 13 P$_b$3 | | 7.77 | 8.82 | 5.14 | | 828 MH$^-$ |
| 14 P$_b$1 | | 7.81 | 8.84 | 5.15 | | 856 MNa$^+$ |

TABLE 5-continued

| * Comp No. Salt Pro-drug a Pro-drug b | Structure | δ ppm | | | | MASS |
|---|---|---|---|---|---|---|
| | | H$^{a}$* | H$^{b}$* | H$^{c}$* | H$^{d}$* | |
| 15 P$_b$2 | [structure] | 7.80 | 8.83 | 5.15 | | 870 MNa$^+$ |
| 16 Fumaric P$_a$12 | [structure] | 7.82 | 8.86 | 5.13 | 4.89 | 786 MH$^-$ |
| 17 P$_a$13 | [structure] | 7.82 | 8.86 | 5.21 | 4.92 | 856 MH$^-$ |
| 18 P$_b$4 | [structure] | 7.80 | 8.83 | 4.98 | | 896 MNa$^+$ |

TABLE 5-continued

| * Comp No. Salt Pro-drug a Pro-drug b | Structure | δ ppm | | | | MASS |
|---|---|---|---|---|---|---|
| | | $H^{a*}$ | $H^{b*}$ | $H^{c*}$ | $H^{d*}$ | |
| 47 Fumaric $P_b6$ | 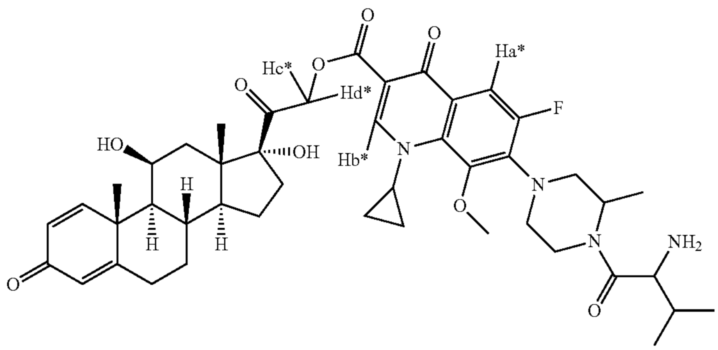 | 7.49 | 8.84 | 5.15 | | 839 $MNa^+$ |
| 48 $P_b7$ TFA | 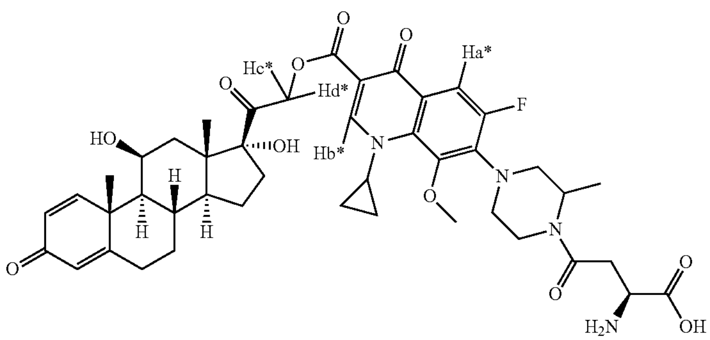 | 7.49 | 8.84 | 5.15 | | n/a |
| 49 $P_b10$ fumaric | 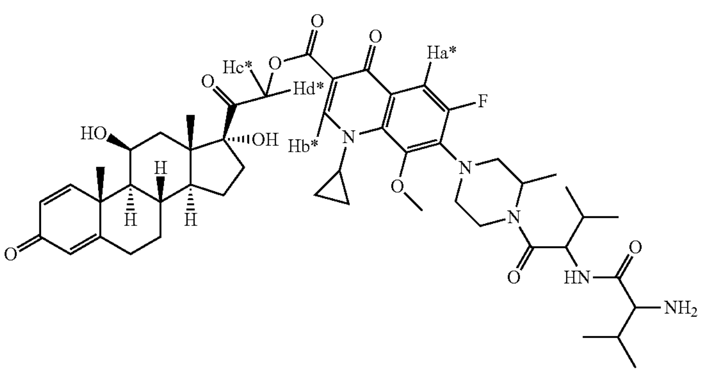 | 7.49 | 8.83 | 5.13 | | 938 $MNa^+$ |
| 50 $P_b9$ fumaric | 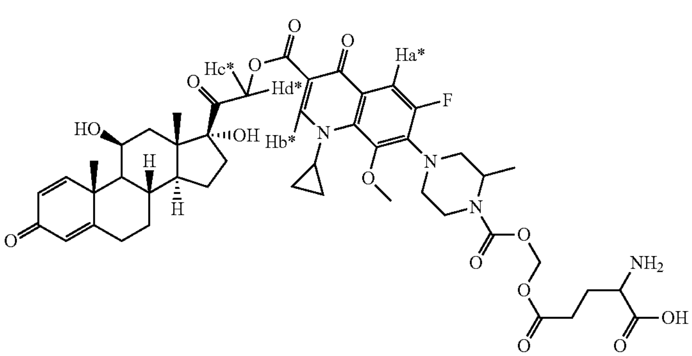 | 7.50 | 8.84 | 5.15 | | 921 $MH^+$ |

TABLE 5-continued
| * Comp No. Salt Pro-drug a Pro-drug b | Structure | δ ppm | | | | MASS |
|---|---|---|---|---|---|---|
| | | $H^{a*}$ | $H^{b*}$ | $H^{c*}$ | $H^{d*}$ | |
| 51 $P_b10$ HCl | 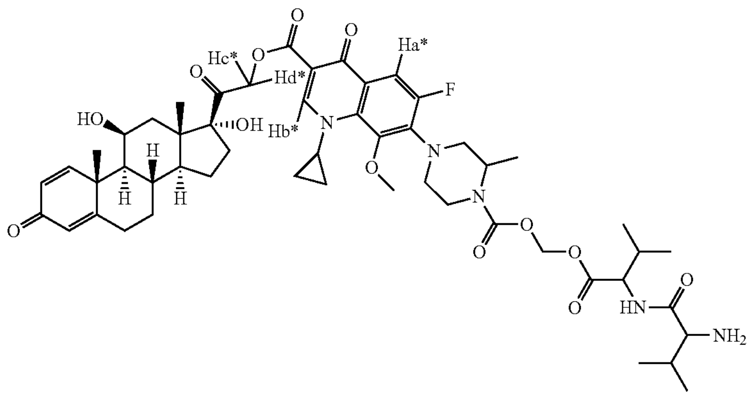 | 7.49 | 9.09 | 5.80 | 5.92 | 990 $MH^+$ |
| 54 $P_b5$ | 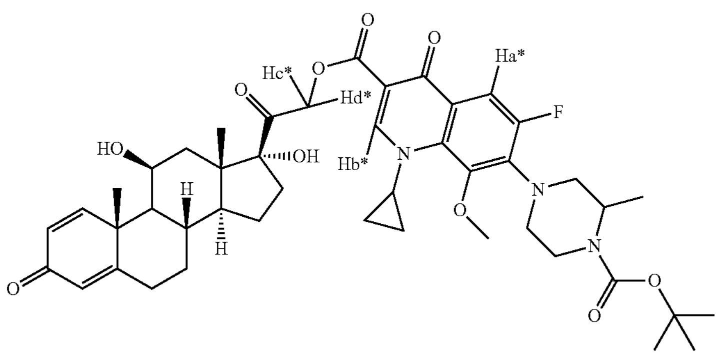 | 7.81 | 8.83 | 5.14 | 5.14 | |
Gatifloxacin reacted with hydrocortisone to form the following hybrid compounds as shown in Scheme 8 with the results shown in Table 6.
Scheme 8
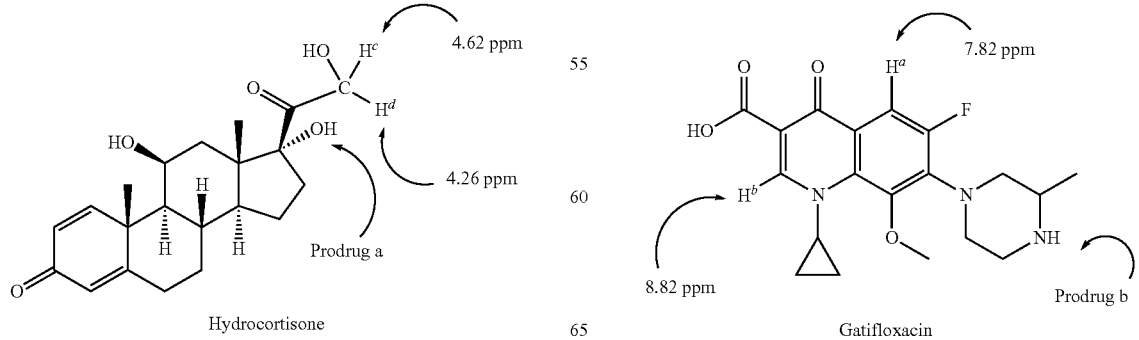

TABLE 6

| *Comp. No. Salt Prodrug a Prodrug b | Structure | δ ppm | | | | MASS |
|---|---|---|---|---|---|---|
| | | H$^{a*}$ | H$^{b*}$ | H$^{c*}$ | H$^{d*}$ | |
| 19 fumaric | 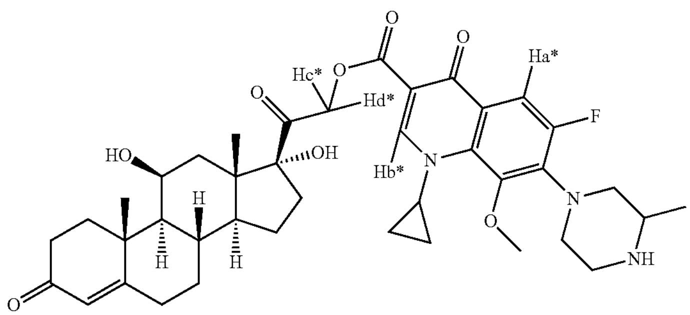 | 7.84 | 8.84 | 5.18 | | 720 MH$^+$ |
| 20 P$_b$3 | 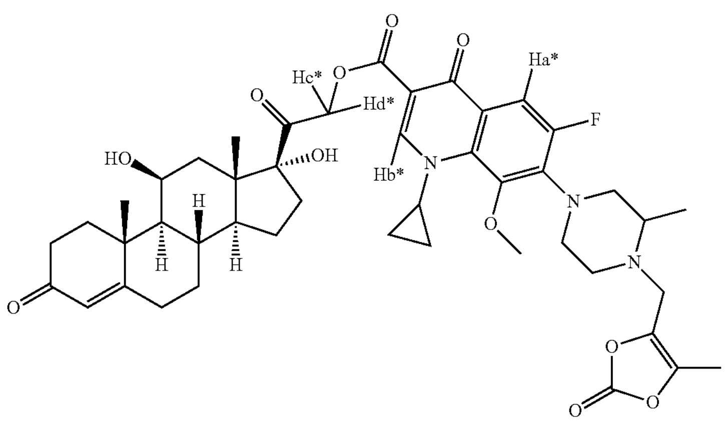 | 7.78 | 8.82 | 5.16 | | 854 MNa$^+$ |
| 21 P$_b$2 | 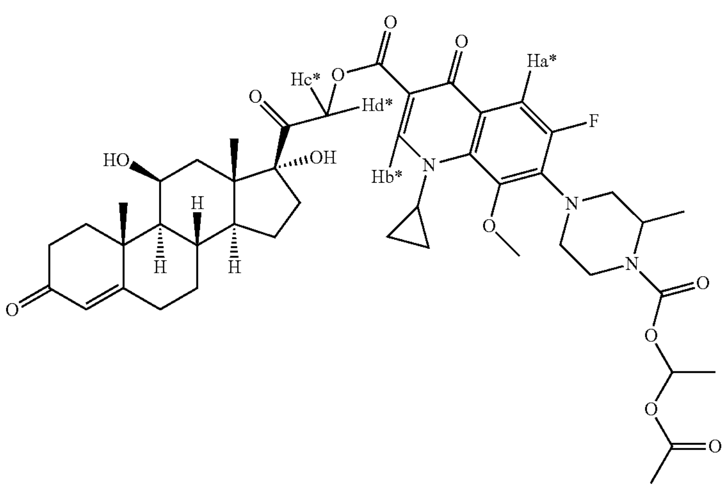 | 7.80 | 8.83 | 5.17 | | 872 MNa$^+$ |

TABLE 6-continued

| *Comp. No. Salt Prodrug a Prodrug b | Structure | δ ppm | | | | MASS |
|---|---|---|---|---|---|---|
| | | H$^{a*}$ | H$^{b*}$ | H$^{c*}$ | H$^{d*}$ | |
| 22 P$_a$13 | 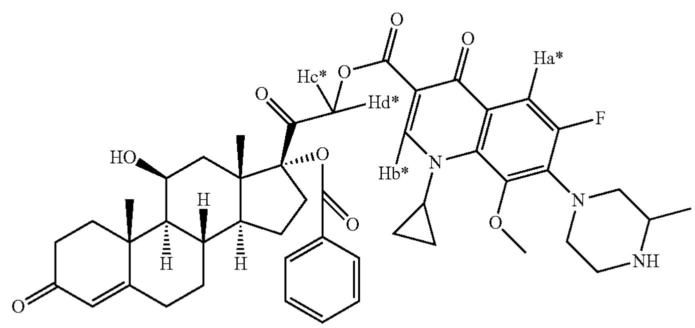 | 8.03 | 8.86 | 5.21 | 4.91 | 822 MH$^-$ |
| 23 P$_b$2 P$_a$13 | 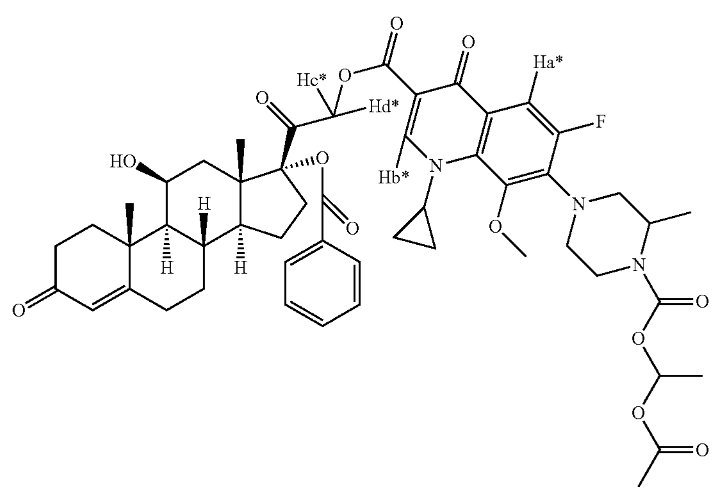 | 7.77 | 8.84 | 5.21 | 4.91 | 977 MNa$^+$ |
| 55 P$_b$5 | 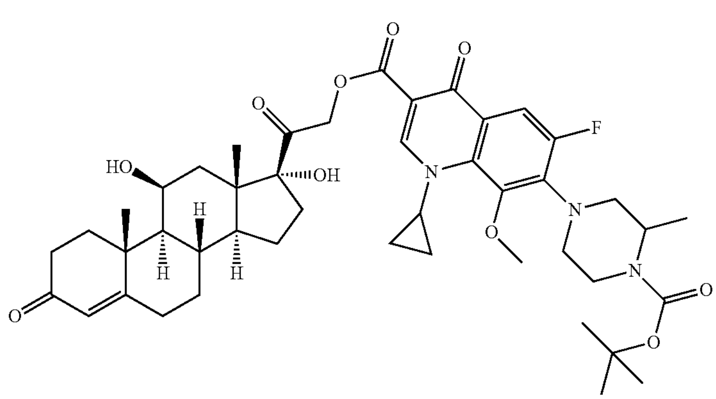 | 7.82 | 8.82 | 5.2 | 5.13 | 842 MNa$^+$ |

Gatifloxacin reacted with triamcinolone acetonide to form the following hybrid compounds as shown in Scheme 9 with the results shown in Table 7.
Scheme 9
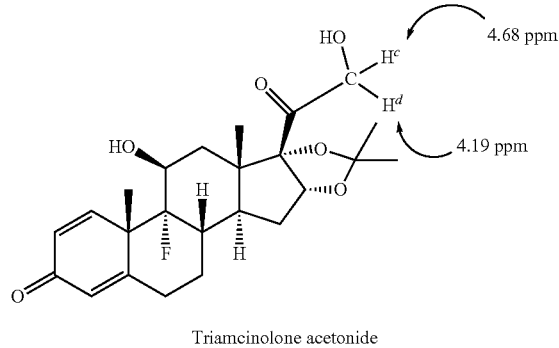
Triamcinolone acetonide
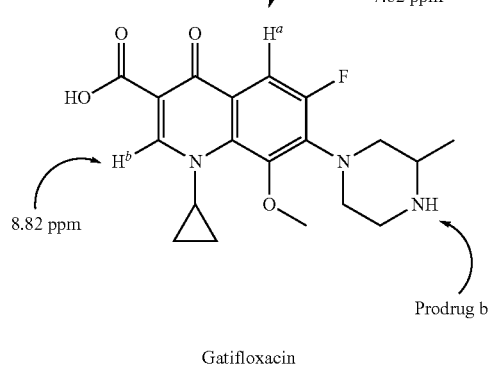
Gatifloxacin
TABLE 7
| *Comp. No. Prodrug b | Structure | δ ppm | | | | MASS |
|---|---|---|---|---|---|---|
| | | H$^{a}$* | H$^{b}$* | H$^{c}$* | H$^{d}$* | |
| 24 P$_b$2 | 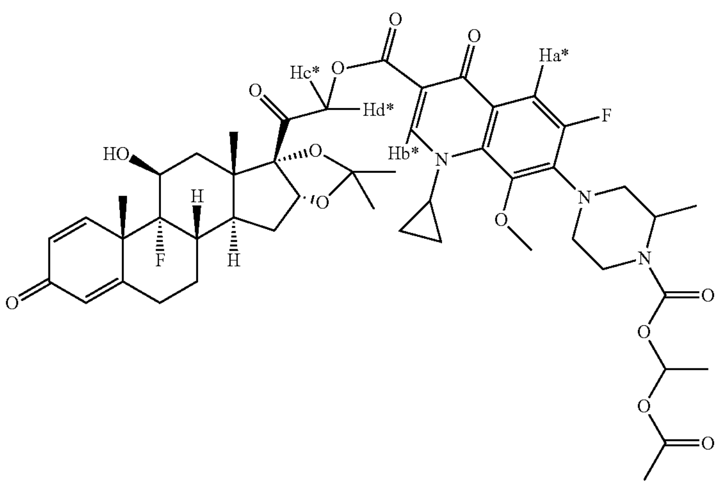 | 7.81 | 8.84 | 5.15 | 5.07 | 944 MNa$^+$ |
| 25 P$_b$3 | 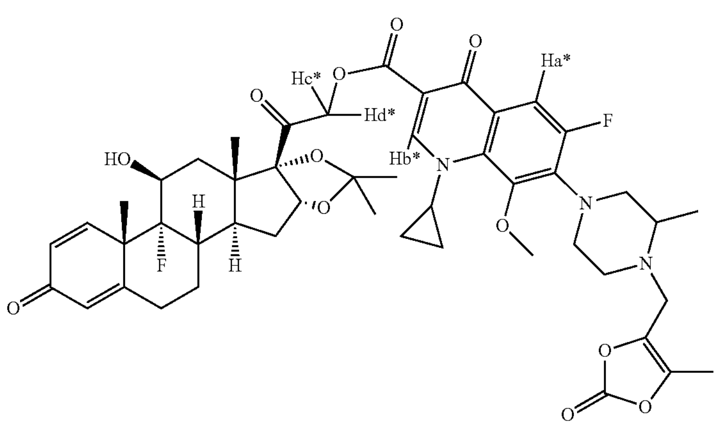 | 7.76 | 8.81 | 5.04 | | 926 MNa$^+$ |

Moxifloxacin reacted with betamethasone to form the following hybrid compounds as shown in Scheme 10 with the results shown in Table 8.
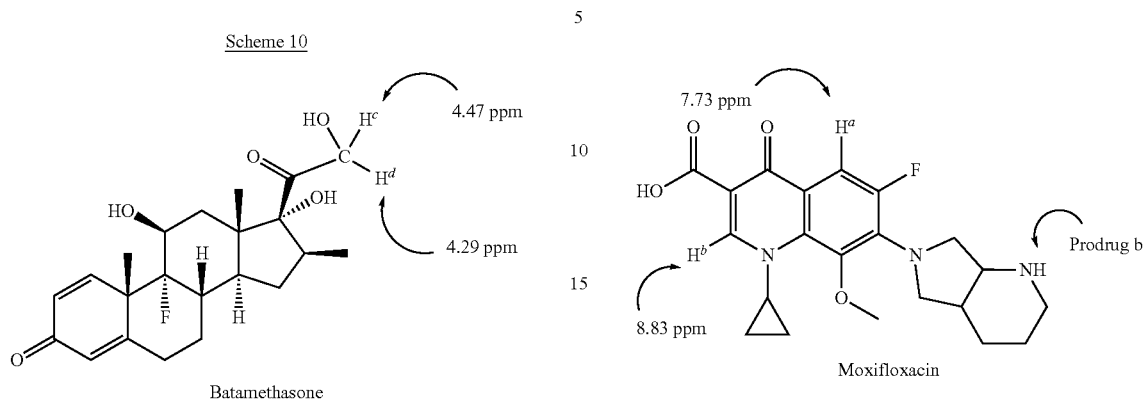
Scheme 10
Batamethasone
Moxifloxacin
Prodrug b
TABLE 8
| * Comp. No. Salt Prodrug b | Structure | δ ppm | | | | MASS |
|---|---|---|---|---|---|---|
| | | H$^{a}$* | H$^{b}$* | H$^{c}$* | H$^{d}$* | |
| 26 fumaric | 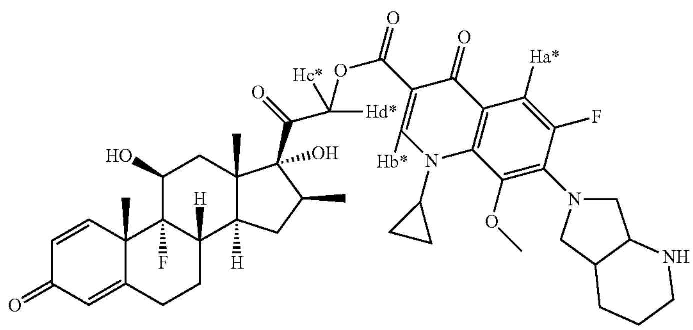 | 7.76 | 8.82 | 5.17 | 5.07 | 776 MH$^+$ |
| 27 P$_b$3 | 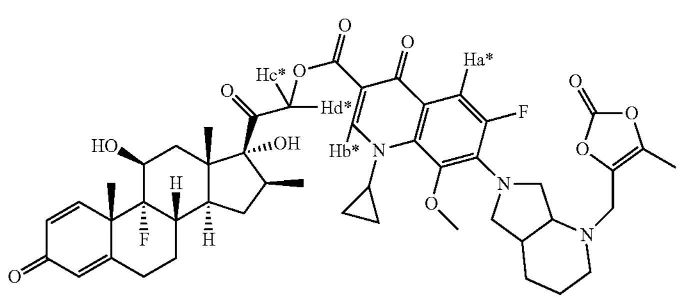 | 7.72 | 8.79 | 5.15 | 5.05 | 910 MNa$^+$ |
| 28 P$_b$1 | 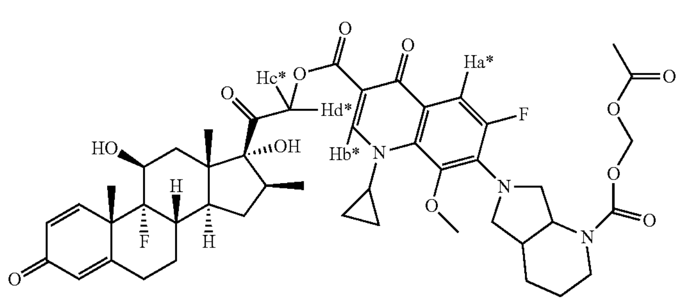 | 7.74 | 8.81 | 5.17 | 5.04 | 914 MNa$^+$ |

TABLE 8-continued
| * Comp. No. Salt Prodrug b | Structure | δ ppm | | | | MASS |
|---|---|---|---|---|---|---|
| | | $H^{a*}$ | $H^{b*}$ | $H^{c*}$ | $H^{d*}$ | |
| 52 $P_b5$ | 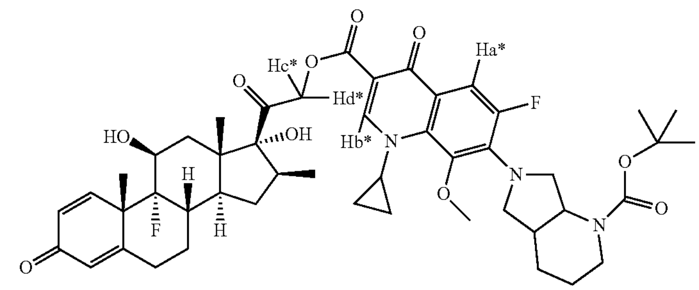 | 7.54 | 8.50 | 5.07 | 4.94 | 898 MNa⁺ |
Moxifloxacin reacted with dexamethasone to form the following hybrid compounds as shown in Scheme 11 with the results shown in Table 9.
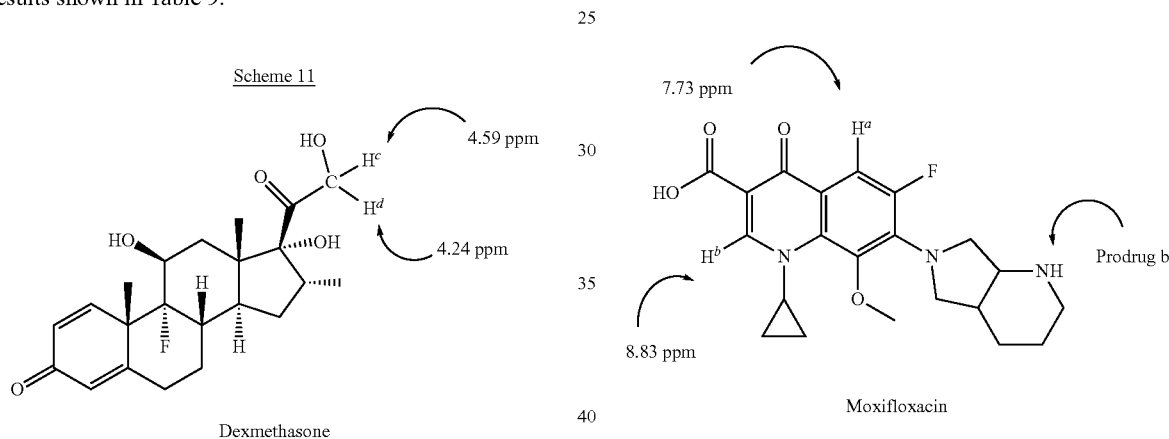
Scheme 11
Dexmethasone
Moxifloxacin
TABLE 9
| * Comp. No. Prodrug b | Structure | δ ppm | | | | MASS |
|---|---|---|---|---|---|---|
| | | $H^{a*}$ | $H^{b*}$ | $H^{c*}$ | $H^{d*}$ | |
| 29 | 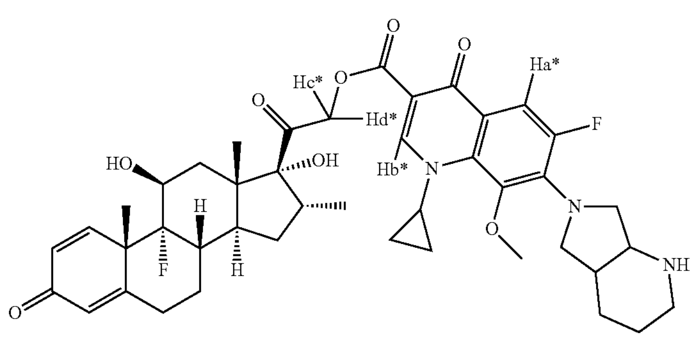 | 7.87 | 9.12 | 5.30 | | 776 MH⁺ |

TABLE 9-continued
| *Comp. No. Prodrug b | Structure | δ ppm | | | | MASS |
|---|---|---|---|---|---|---|
| | | H$^{a*}$ | H$^{b*}$ | H$^{c*}$ | H$^{d*}$ | |
| 30 P$_b$3 | 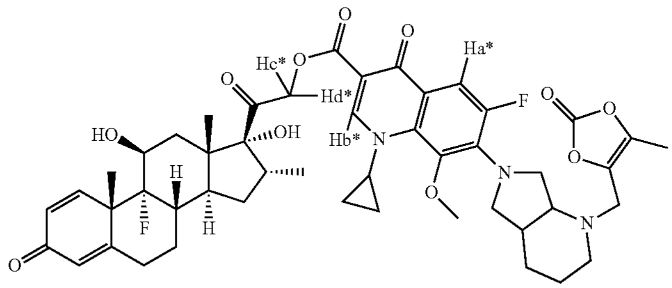 | 7.72 | 8.80 | 5.16 | 5.08 | 910 MNa$^+$ |
| 31 P$_b$1 | 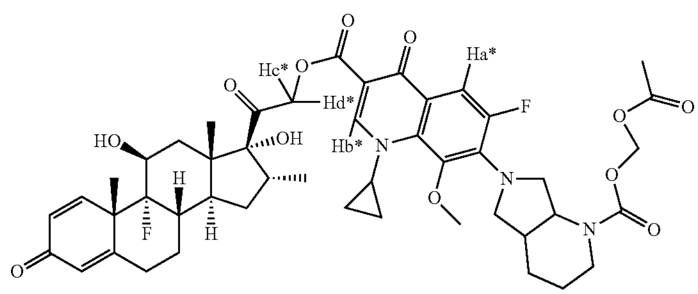 | 7.73 | 8.81 | 5.16 | 5.07 | 890 MH$^+$ |
Moxifloxacin reacted with prednisolone to form the following hybrid compounds as shown in Scheme 12 with the results shown in Table 10.
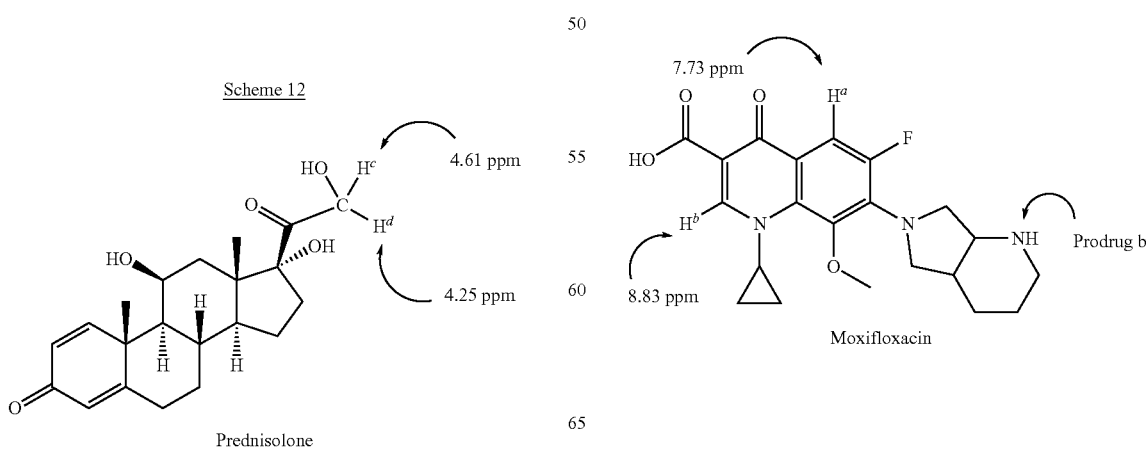
Scheme 12

TABLE 10
| *Comp. No. Salt Pro-drug b | Structure | δ ppm | | | | MASS |
|---|---|---|---|---|---|---|
| | | H$^{a*}$ | H$^{b*}$ | H$^{c*}$ | H$^{d*}$ | |
| 32 fumaric | 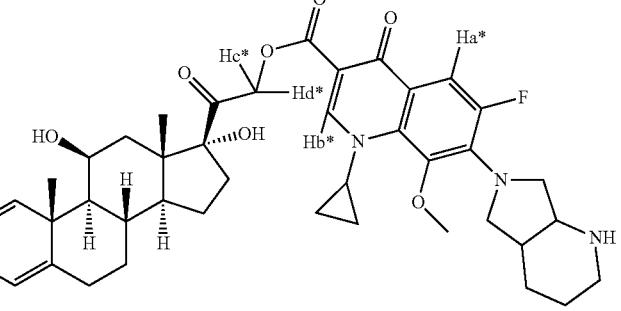 | 7.73 | 8.82 | 5.14 | | 744 MH$^+$ |
| 33 P$_b$3 | 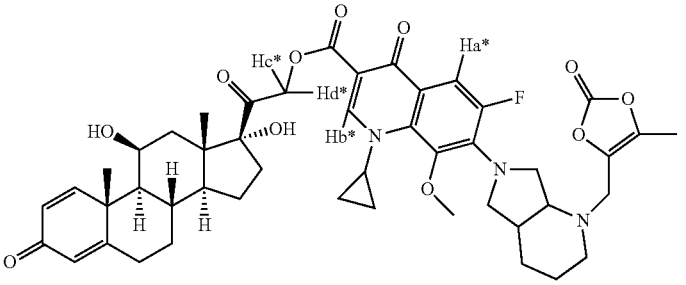 | 7.69 | 8.78 | 5.13 | | 878 MNa$^+$ |
| 34 P$_b$1 | 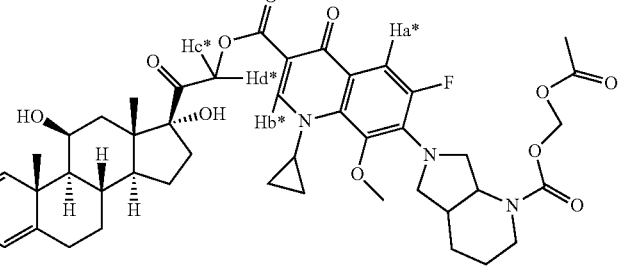 | 7.69 | 8.78 | 5.13 | | 882 MNa$^+$ |
| 53 P$_b$5 | 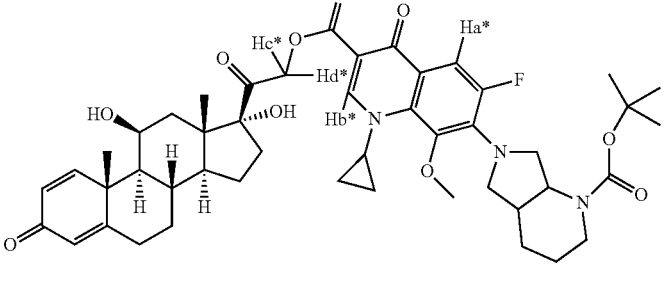 | 7.73 | 8.79 | 5.13 | 5.13 | 866 MNa$^+$ |

Moxifloxacin reacted with hydrocortisone to form the following hybrid compounds as shown in Scheme 13 with the results shown in Table 11.
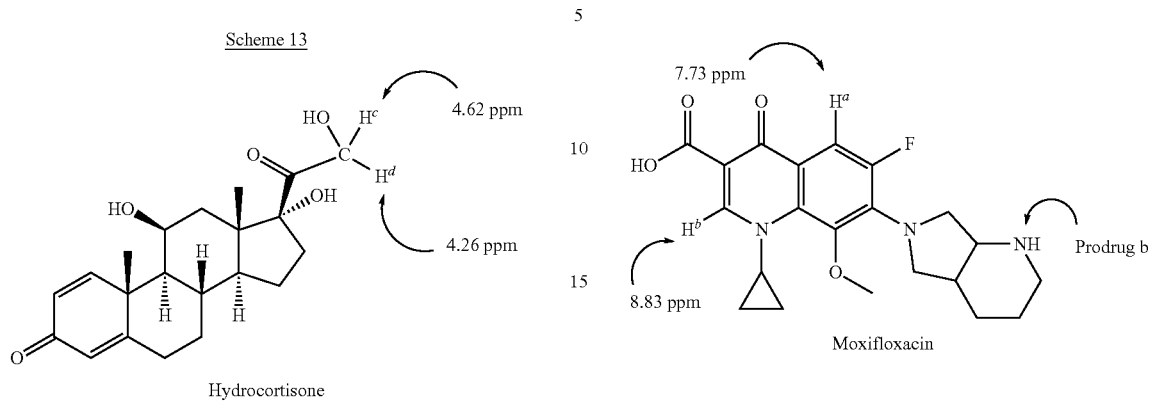
Scheme 13
Hydrocortisone
Moxifloxacin
Prodrug b
TABLE 11
| * Comp. No. Salt Prodrug b | Structure | δ ppm | | | | MASS |
|---|---|---|---|---|---|---|
| | | H$^{a*}$ | H$^{b*}$ | H$^{c*}$ | H$^{d*}$ | |
| 35 fumaric | 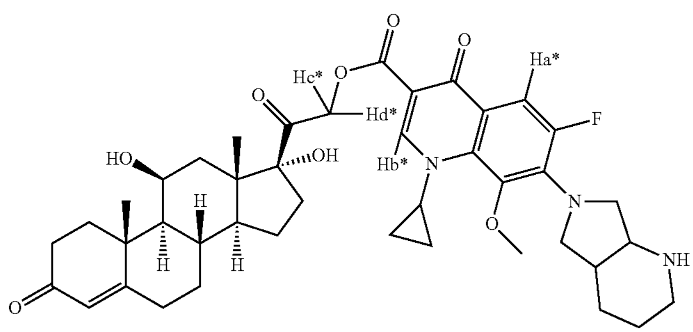 | 7.69 | 8.81 | 5.22 | 5.13 | 746 MH$^+$ |
| 36 P$_b$3 | 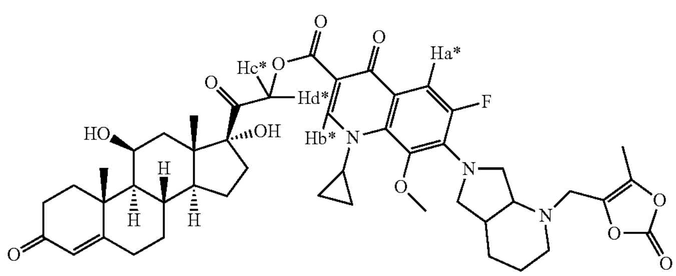 | 7.72 | 8.79 | 5.16 | | 856 MH$^-$ |
| 37 P$_b$1 | 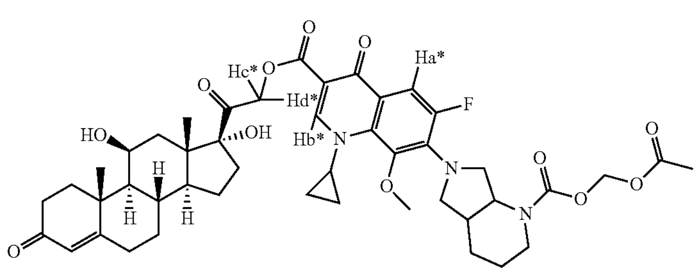 | 7.72 | 8.80 | 5.16 | | 884 MNa$^+$ |

Moxifloxacin reacted with triamcinolone acetonide to form the following hybrid compounds as shown in Scheme 14 with the results shown in Table 12.

Besifloxacin reacted with betamethasone to form the following hybrid compounds as shown in Scheme 15 with the results shown in Table 13.

Scheme 14

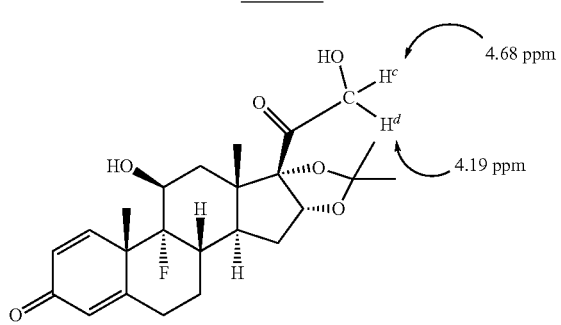

Triamcinolone acetonide

Scheme 15

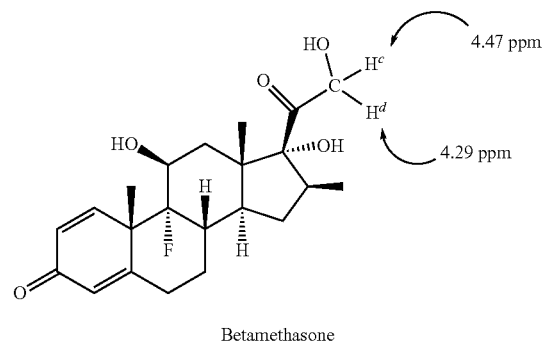

Betamethasone

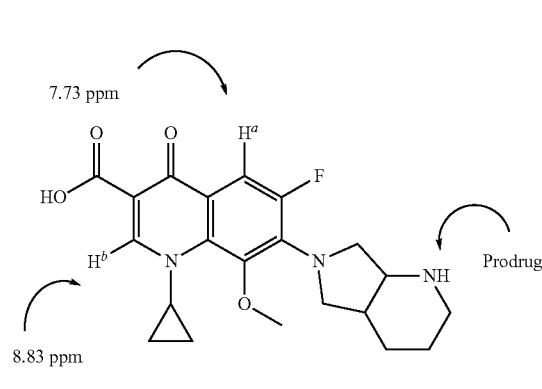

Moxifloxacin

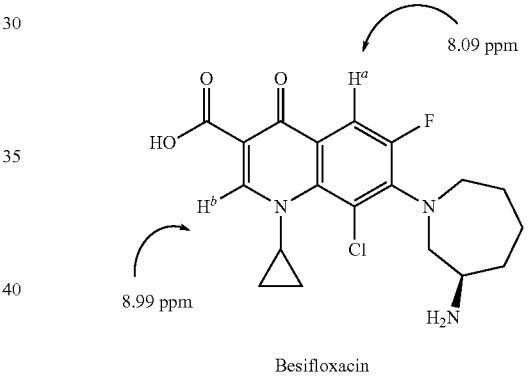

Besifloxacin

TABLE 12

| *Comp. No. Prodrug | Structure | δ ppm | | | | MASS |
| --- | --- | --- | --- | --- | --- | --- |
| | | $H^{a*}$ | $H^{b*}$ | $H^{c*}$ | $H^{d*}$ | |
| 38 P3 | 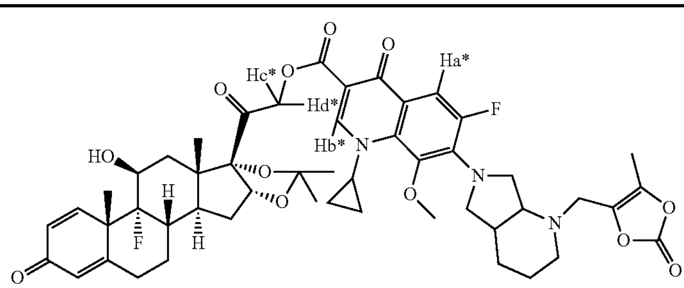 | 7.71 | 8.79 | 5.27 | 5.05 | 931 MH+ |

TABLE 13
| * Comp. No. Salt | Structure | δ ppm | | | MASS |
|---|---|---|---|---|---|
| | | $H^{a}*$ | $H^{b}*$ | $H^{c}*$ | |
| 39 fumaric | (structure shown) | 7.93 | 8.95 | 5.16 | 769 $MH^+$ |
Besifloxacin reacted with dexamethasone to form the following hybrid compounds as shown in Scheme 16 with the results shown in Table 14.
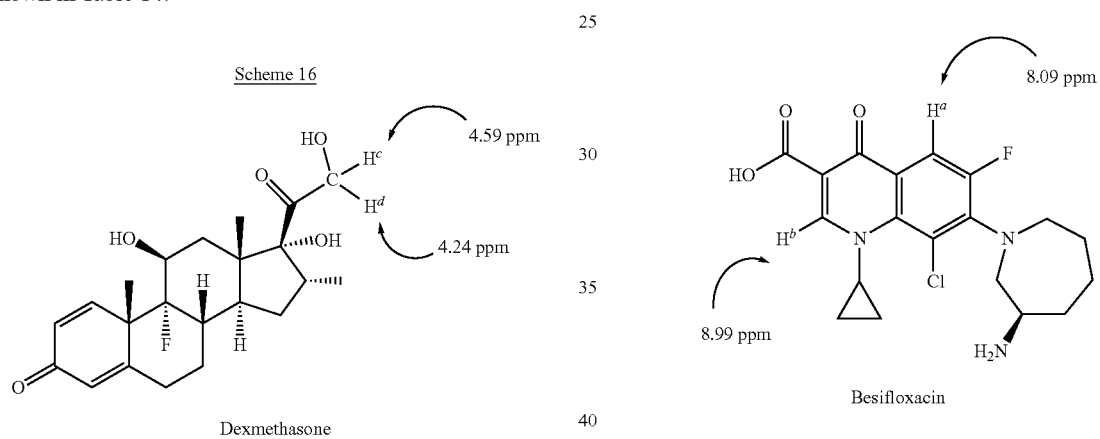
Scheme 16
Dexmethasone
Besifloxacin
TABLE 14
| * Comp. No. Salt | Structure | δ ppm | | | MASS |
|---|---|---|---|---|---|
| | | $H^{a}*$ | $H^{b}*$ | $H^{c}*$ | |
| 40 fumaric | (structure shown) | 7.93 | 8.94 | 5.17 | 769 $MH^+$ |

Besifloxacin reacted with prednisolone to form the following hybrid compounds as shown in Scheme 17 with the results shown in Table 15.
Besifloxacin reacted with hydrocortisone to form the following hybrid compounds as shown in Scheme 18 with the results shown in Table 16.
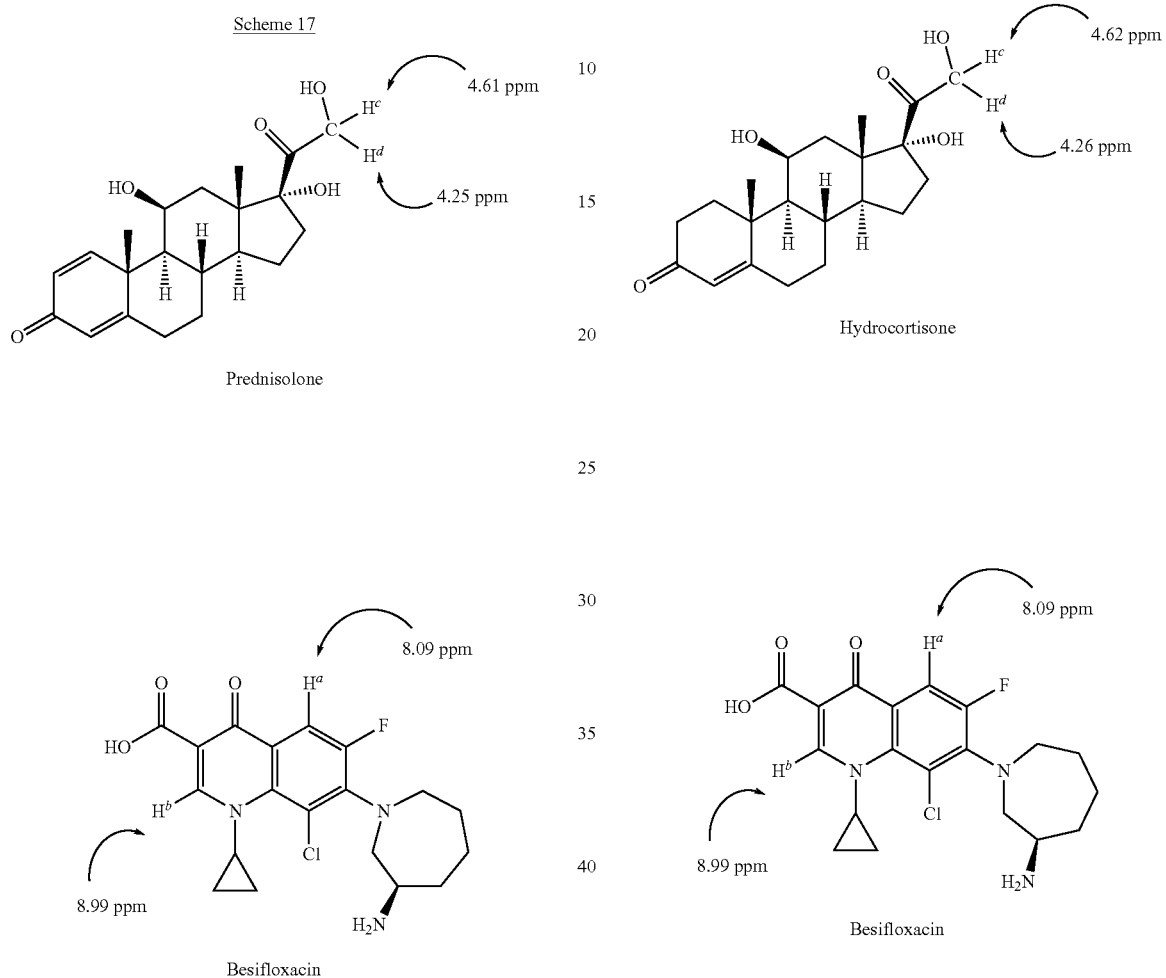
TABLE 15
| *Comp. No. Salt | Structure | δ ppm $H^{a}*$ | $H^{b}*$ | $H^{c}*$ | MASS |
|---|---|---|---|---|---|
| 41 fumaric | 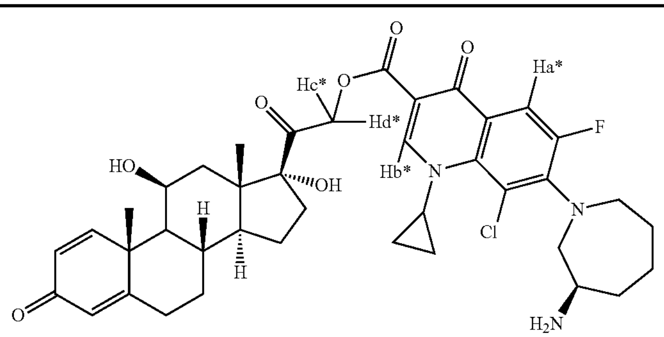 | 8.04 | 8.96 | 5.17 | 737 $MH^+$ |

TABLE 16
| *Comp. No. Salt | Structure | δ ppm $H^{a}*$ | $H^{b}*$ | $H^{c}*$ | MASS |
|---|---|---|---|---|---|
| 42 fumaric | 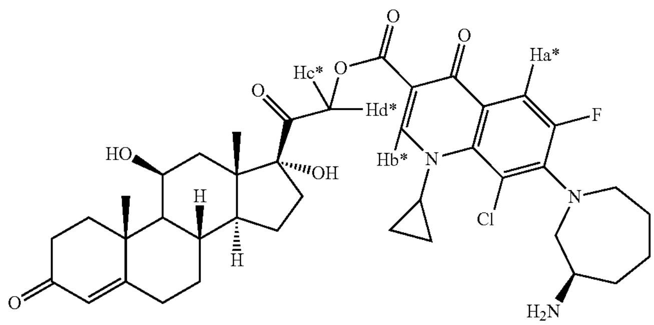 | 8.04 | 8.96 | 5.19 | 739 MH+ |
Betamethasone reacted with levofloxacin to form the following hybrid compounds as shown in Scheme 18a with the results shown in Table 17.
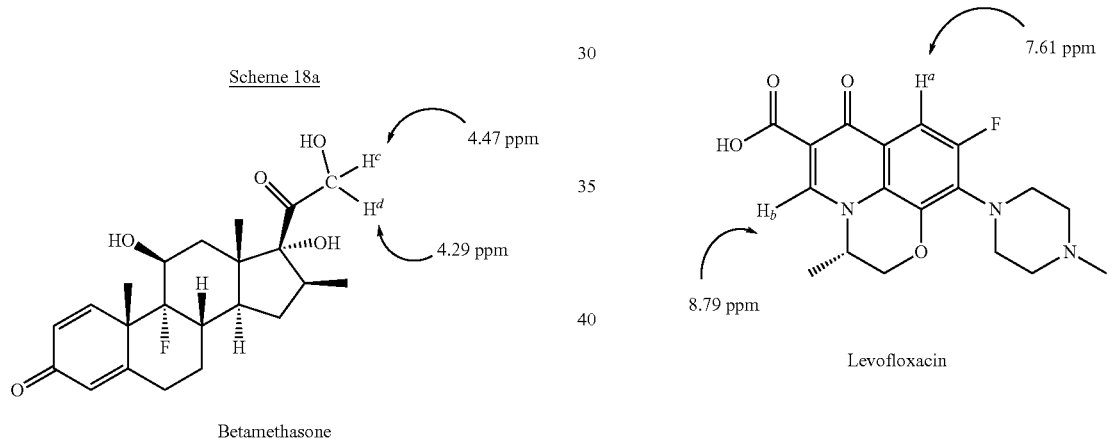
Scheme 18a
TABLE 17
| *Comp. No. | Structure | δ ppm $H^{a}*$ | $H^{b}*$ | $H^{c}*$ | $H^{d}*$ | MASS |
|---|---|---|---|---|---|---|
| 43 | 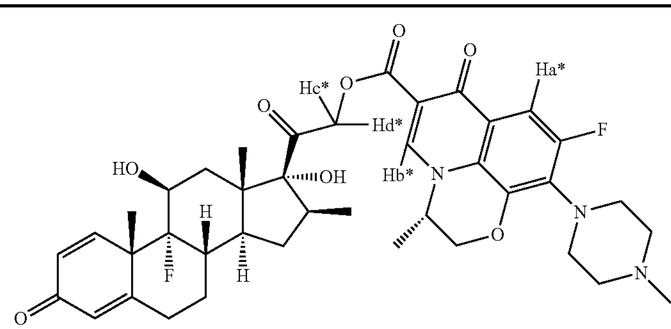 | 7.81 | 8.84 | 5.16 | 5.07 | 736 MH+ |

Dexamethasone reacted with levofloxacin to form the following hybrid compounds as shown in Scheme 19 with the results shown in Table 18.

Prednisolone reacted with levofloxacin to form the following hybrid compounds as shown in Scheme 20 with the results shown in Table 19.

Scheme 19

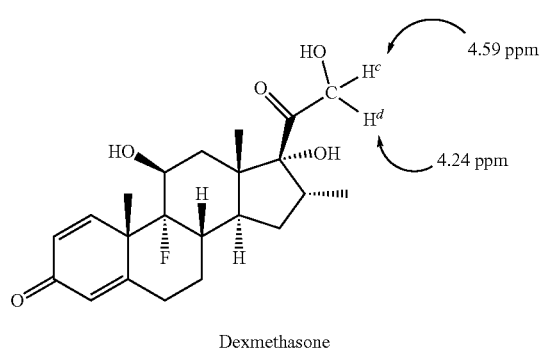

Dexmethasone

Scheme 20

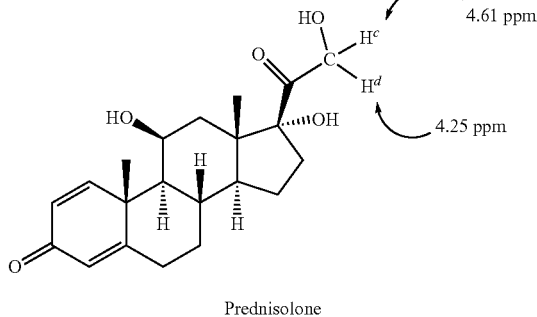

Prednisolone

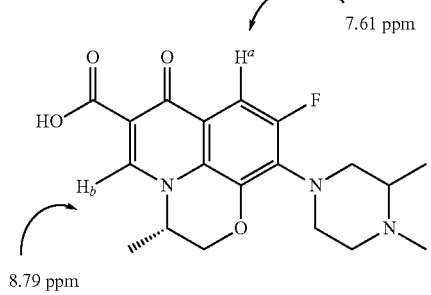

Levofloxacin

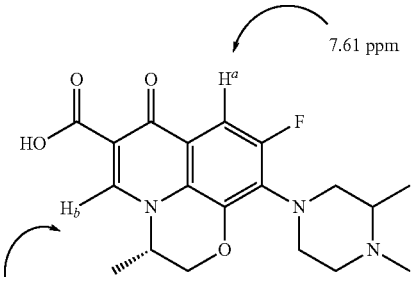

Levofloxacin

TABLE 18

| Comp. No. | Structure | $H^{a}$* | $H^{b}$* | $H^{c}$* | $H^{d}$* | MASS |
|---|---|---|---|---|---|---|
| 44 | 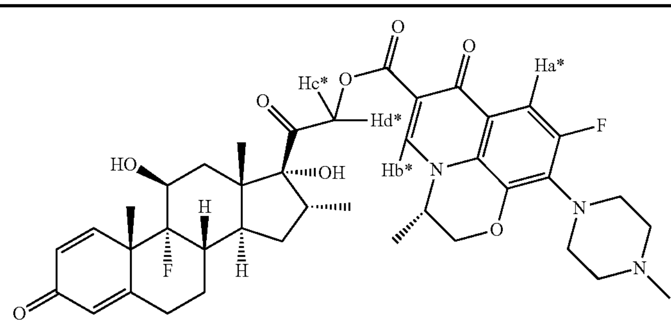 | 7.55 | 8.78 | 5.17 | 5.07 | 736 MH$^+$ |

TABLE 19
| *Comp. No. Salt | Structure | δ ppm H$^{a}$* | H$^{b}$* | H$^{c}$* | MASS |
|---|---|---|---|---|---|
| 45 fumaric | 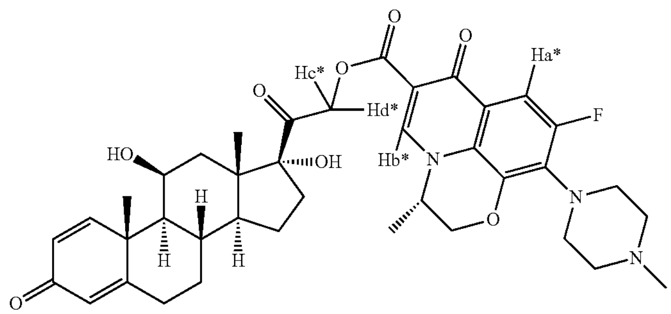 | 7.51 | 8.81 | 5.14 | 704 MH$^+$ |
Hydrocortisone reacted with levofloxacin to form the following hybrid compounds as shown in Scheme 21 with the results shown in Table 20.
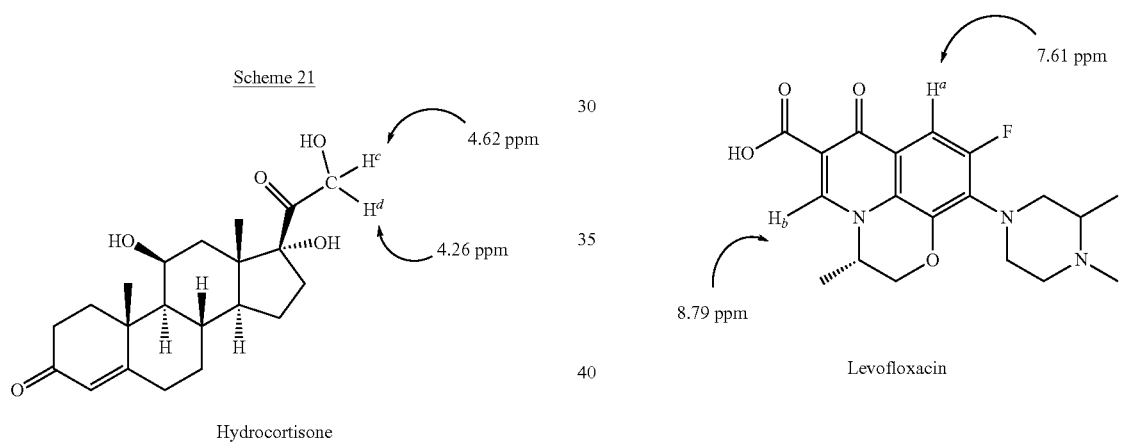
Scheme 21
Hydrocortisone
Levofloxacin
TABLE 20
| *Comp. No. | Structure | δ ppm H$^{a}$* | H$^{b}$* | H$^{c}$* | MASS |
|---|---|---|---|---|---|
| 46 | 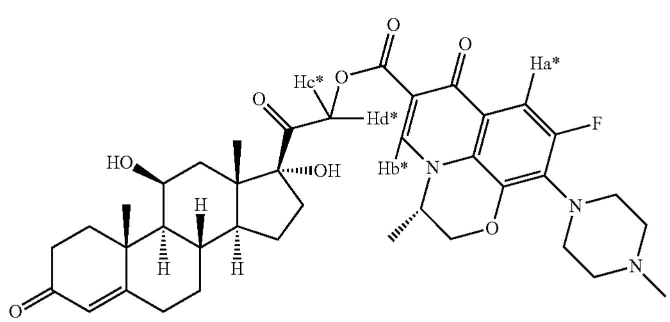 | 7.53 | 8.77 | 5.16 | 706 MH$^+$ |

BIOLOGICAL EXAMPLES

Example 1

In Vitro Metabolic Stability in Rabbit Cornea Homogenates and Human Recombinant Carboxylesterases Dutch Belted rabbits were euthanized with an overdose of sodium pentobarbital. The corneas were collected and homogenized in ice-cold potassium chloride solution (pH=7.4). The homogenate was centrifuged at 755×g for 30 min at 4° C. and aliquots of the supernatant were stored at or below −70° C. until metabolism experiments were conducted. Prior to storing the homogenates an aliquot was removed for determination of protein concentrations by calculating the 260 nm absorbance using a spectrophotometer. Human recombinant carboxylesterases were purchased from a commercial vendor (BD Gentest™, Bedford, Mass.)

All metabolic stability experiments were performed in triplicate in 96-well plate format. The final incubation mixture contained 1 μM test compound, 0.3 mg/mL corneal protein homogenate or 0.1 mg/mL human recombinant carboxylesterase mixture in a final volume of 0.5 mL 0.1M potassium phosphate buffer (pH=6.0). The final percentage of solvent in the incubation was less than 1.0% to prevent inhibition of enzymatic activity. Following a pre-incubation at 37° C., test article was added to initiate the reaction. At designated time points (typically less than 60 minutes to capture the linear range of metabolite formation), 0.05 mL aliquots were removed from the incubation mixtures using a clean pipet tip and immediately placed in organic solvent to stop any esterase activity. The hydrolysis to the metabolites was confirmed to be due to esterase activity and not chemical lability.

The samples were analyzed by liquid chromatography with mass spectrometry (LC-MS/MS) detection to determine the metabolite concentrations resulting from the metabolism of the hybrid compounds. Internal standards were used to compensate for variability from sample processing, chromatographic elution, mass spectrometer response and ion suppression by matrix components.

Results

Table 21 lists the rate of metabolite formation in rabbit cornea homogenates

TABLE 21

| Comp. No. | IUPAC Name | Rate of formation Metabolite 1 (nM/min/mg) | Rate of formation Metabolite 2 (nM/min/mg) |
|---|---|---|---|
| 1 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate | 7.27 ± 0.58 Betamethasone | 4.45 ± 0.28 Gatifloxacin |
| 7 | 2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate | 7.31 ± 0.62 Dexamethasone | 4.93 ± 0.48 Gatifloxacin |
| 12 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate | 6.02 ± 0.63 Prednisolone | 3.46 ± 0.50 Gatifloxacin |

Table 22 Lists the rate of metabolite formation in human recombinant carboxylesterases

TABLE 22

| Comp. No. | IUPAC Name | Rate of formation Metabolite 1 (nM/min/mg) | Rate of formation Metabolite 2 (nM/min/mg) |
|---|---|---|---|
| 1 | 2-[(8R,9S,10R,11R,13R,14R,16R,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate | 63.4 ± 4.4 Betamethasone | 34.6 ± 2.5 Gatifloxacin |

TABLE 22-continued

| Comp. No. | IUPAC Name | Rate of formation Metabolite 1 (nM/min/mg) | Rate of formation Metabolite 2 (nM/min/mg) |
|---|---|---|---|
| 7 | 2-[(8R,9S,10R,11R,13R,14R,16S,17S)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate | 26.6 ± 0.5 Dexamethasone | 17.2 ± 0.5 Gatifloxacin |
| 12 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate | 130 ± 10 Prednisolone | 72.7 ± 6.4 Gatifloxacin |
| 22 | 2-{(8R,10S,11R,13R,14R,17S)-11-hydroxy-10,13-dimethyl-3-oxo-17-[(phenylcarbonyl)oxy]-2,3,6,7,8,9,10,11,12,13,14,15,16,17-tetradecahydro-1H-cyclopenta[a]phenanthren-17-yl}-2-oxoethyl rel-1-cyclopropyl-6-fluoro-8-methoxy-7-(3-methylpiperazin-1-yl)-4-oxo-1,4-dihydroquinoline-3-carboxylate | 21.4 ± 1.07 Hydrocortisone | 3.99 ± 0.33 Gatifloxacin |
| 5 | 2-[(8R,9S,10R,11R,13R,14R,16R,17S)-17-(acetyloxy)-9-fluoro-11-hydroxy-10,13,16-trimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-(3-methylpiperazin-1-yl)-4-oxo-1,4-dihydroquinoline-3-carboxylate | 1.81 ± 0.09 Betamethasone | 1.11 ± 0.07 Gatifloxacin |
| 41 | 2-[(8R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-[(3S)-3-aminoazepan-1-yl]-8-chloro-1-cyclopropyl-6-fluoro-4-oxo-1,4-dihydroquinoline-3-carboxylate | 312 ± 12 Prednisolone | 286 ± 31 Besifloxacin |
| 45 | 2-[(8R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-(3R)-9-fluoro-3-methyl-10-(4-methylpiperazin-1-yl)-7-oxo-2,3-dihydro-7H-[1,4]oxazino[2,3,4-ij]quinoline-6-carboxylate | 1.53 ± 0.19 Prednisolone | 2.07 ± 1.91 Levofloxacin |
| 15 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-(4-{[1-(acetyloxy)ethoxy]carbonyl}-3-methylpiperazin-1-yl)-1-cyclopropyl-6-fluoro-8-methoxy-4-oxo-1,4-dihydroquinoline-3-carboxylate | 119 ± 5 Gatifloxacin | 118 ± 8 Prednisolone |
| 13 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-{3-methyl-4-[(5-methyl-2-oxo-1,3-dioxol-4-yl)methyl]piperazin-1-yl}-4-oxo-1,4-dihydroquinoline-3-carboxylate | 465 ± 18 Gatifloxacin | 565 ± 47 Prednisolone |

TABLE 22-continued

| Comp. No. | IUPAC Name | Rate of formation Metabolite 1 (nM/min/mg) | Rate of formation Metabolite 2 (nM/min/mg) |
|---|---|---|---|
| 14 | 2-[(8R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-7-(4-{[(acetyloxy)methoxy]carbonyl}-3-methylpiperazin-1-yl)-1-cyclopropyl-6-fluoro-8-methoxy-4-oxo-1,4-dihydroquinoline-3-carboxylate | 53.7 ± 5.5 Gatifloxacin | 52.0 ± 7.2 Prednisolone |
| 21 | 2-[(10R,11S,13S,17R)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-7-(4-{[1-(acetyloxy)ethoxy]carbonyl}-3-methylpiperazin-1-yl)-1-cyclopropyl-6-fluoro-8-methoxy-4-oxo-1,4-dihydroquinoline-3-carboxylate | 143 ± 30 Hydrocortisone | 148 ± 19 Gatifloxacin |
| 20 | 2-[(8R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-1-cyclopropyl-6-fluoro-8-methoxy-7-{3-methyl-4-[(5-methyl-2-oxo-1,3-dioxol-4-yl)methyl]piperazin-1-yl}-4-oxo-1,4-dihydroquinoline-3-carboxylate | 828 ± 60 Hydrocortisone | 818 ± 97 Gatifloxacin |
| 33 | 2-[(8R,9R,10S,11R,13R,14R,17S)-11,17-dihydroxy-10,13-dimethyl-3-oxo-6,7,8,9,10,11,12,13,14,15,16,17-dodecahydro-3H-cyclopenta[a]phenanthren-17-yl]-2-oxoethyl rel-1-cyclopropyl-6-fluoro-8-methoxy-7-{1-[(5-methyl-2-oxo-1,3-dioxol-4-yl)methyl]octahydro-6H-pyrrolo[3,4-b]pyridin-6-yl}-4-oxo-1,4-dihydroquinoline-3-carboxylate | 85.2 ± 11.6 Prednisolone | 85.8 ± 12.6 Moxifloxacin |
| 36 | 2-[(8R,9R,10S,11R,13R,14R,17S)-11,17-dihydroxy-10,13-dimethyl-3-oxo-2,3,6,7,8,9,10,11,12,13,14,15,16,17-tetradecahydro-1H-cyclopenta[a]phenanthren-17-yl]-2-oxoethyl rel-1-cyclopropyl-6-fluoro-8-methoxy-7-{1-[(5-methyl-2-oxo-1,3-dioxol-4-yl)methyl]octahydro-6H-pyrrolo[3,4-b]pyridin-6-yl}-4-oxo-1,4-dihydroquinoline-3-carboxylate | 48.3 ± 37.9 Hydrocortisone | 45.1 ± 34.8 Moxifloxacin |

The data demonstrate that direct linkage of a fluoroquinolone (e.g. gatifloxacin, moxifloxacin, besifloxacin, and levofloxacin) and a steroid (e.g. hydrocortisone, betamethasone, dexamethasone and prednisolone) as a single hybrid compound was hydrolyzed enzymatically in rabbit cornea homogenates and human recombinant carboxylesterases to their respective individual antibiotic and steroid drugs.

Example 2

In Vitro Corneal Permeability and Metabolic Stability in Human Corneal Epithelial Cells Clonetics® human corneal epithelial cells (HCEC) were purchased from Lonza Walkersville, Inc. (Walkersville, Md.) pre-seeded on Costar Transwell™ filters in a 24-well plate. Upon receipt HCEC cells were cultured overnight in a 37° C. incubator (95% $O_2$, 5% $CO_2$) in media provided by the vendor. Permeability studies were performed within 24 hours of receipt. Dosing solutions 100 μM test article (i.e. ester linked hybrids) were prepared in Lonza's proprietary media by diluting a 50 mM stock solution of the test article in dimethyl sulfoxide. The final percentage of solvent in the incubation was less than 1.0% to prevent inhibition of enzymatic activity or effects on the cell membrane. Transepithelial electrical resistance (TEER) was measured for all wells using a voltohmmeter with STX-2 electrodes (World Precision Instruments Inc., Sarasota, Fla.) after adding 100 μL pre-warmed (37° C.) media to the apical compartment. All permeability experiments were performed in triplicate by adding 100 μL of the 100 μM dosing solution to the apical compartment of each well (final incubation concentration of 50 μM). After a 2 hour incubation, aliquots of medium from the basolateral compartment of each well were removed to assess permeability. Aliquots of the dosing solution from the apical compartment of each well were collected at the end of incubation to assess mass balance. A final TEER value was measured and recorded for all wells.

To evaluate human corneal epithelial cell integrity, incubations were conducted using 2 μCi/mL $^3$H-mannitol for the same 2 hour incubation period with aliquots taken from the basolateral compartment. $^3$H-Mannitol samples were analyzed using liquid scintillation counting. All ester linked hybrids samples were analyzed by liquid chromatography with mass spectrometry (LC-MS/MS) detection to determine the parent (i.e., ester linked hybrids) and metabolite (i.e. steroid and antibiotic) concentrations resulting from the metabolism of ester linked hybrids. Internal standards were used to compensate for variability from sample processing, chromatographic elution, mass spectrometer response and ion suppression by matrix components.

FIG. 1 shows the cellular uptake of ester linked hybrid (parent) compounds and the hydrolyzed metabolites (steroid and antibiotic) after a two hour incubation with Human Corneal Epithelial Cells. The data demonstrated that direct linkage of a fluoroquinolone (e.g. gatifloxacin, moxifloxacin, and besifloxacin) and a steroid (e.g. hydrocortisone, betamethasone, dexamethasone and prednisolone) as a single hybrid compound was taken up into human corneal epithelial cells and enzymatically hydrolyzed to the individual antibiotic and steroid.

Example 3

Ocular Pharmacokinetics of Compound 12 Following a Single Topical Ophthalmic Administration in New Zealand White Rabbits Rabbits were dosed once by ocular instillation to both eyes with each compound formulated in a 0.4% (w/v) solution. At 0.25, 0.5, 1, 2, 6, and 10 hours post dose cornea, aqueous humor, conjunctiva and eyelid margin were collected and stored at approximately −70° C. until bioanalysis. Ocular tissue samples were analyzed by liquid chromatography with mass spectrometry (LC-MS/MS) detection to determine the parent (i.e., ester linked hybrids) and metabolite (i.e. steroid and antibiotic) concentrations resulting from the metabolism of ester linked hybrids. Internal standards were used to compensate for variability from sample processing, chromatographic elution, mass spectrometer response and ion suppression by matrix components.

Figure 2:
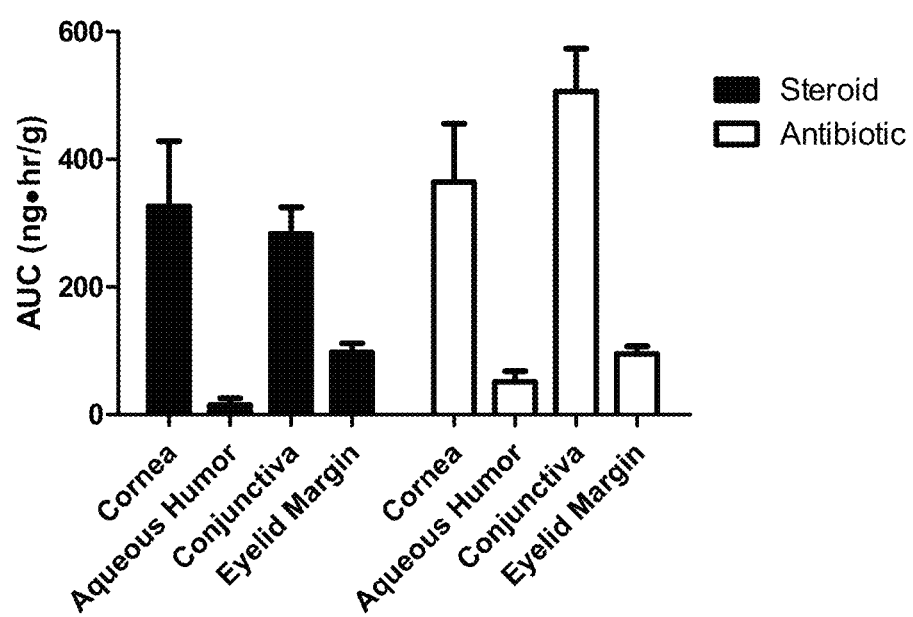
FIG. 2 Shows the mean±standard error of the enzymatically cleaved Prednisolone (steroid) and Gatifloxacin (antibiotic) area under the concentration-time profile ($AUC_{0-10hr}$) Following a Single Topical Ocular Dose of 0.4% of the Hybrid Compound 1210 hr, in Rabbits.

FIG. 2 shows the mean±standard error of the enzymatically cleaved Prednisolone (steroid) and Gatifloxacin (antibiotic) area under the concentration-time profile ($AUC_{0-10hr}$) Following a Single Topical Ocular Dose of 0.4% of the Hybrid Compound 1210 hr, in Rabbits. The data demonstrated that direct linkage of an antibiotic (e.g. gatifloxacin) and a steroid (e.g. prednisolone) as a single hybrid compound was taken up into rabbit ocular tissues and enzymatically hydrolyzed to the individual antibiotic and steroid. This animal study showed that these hybrid compounds have the capability to penetrate ocular tissues and get cleaved to the active metabolites to be clinically effective in treating inflammatory and infectious diseases.

What is claimed is:

1. A hybrid drug comprising one antibiotic moiety and one steroid moiety, or a pharmaceutical salt thereof, which are connected covalently via a linker, wherein the bond is an ester bond or an amide bond, and wherein the antibiotic moiety is a gatifloxacin moiety and the steroid moiety is a prednisolone moiety.

2. The hybrid drug of claim 1, having the following structure:

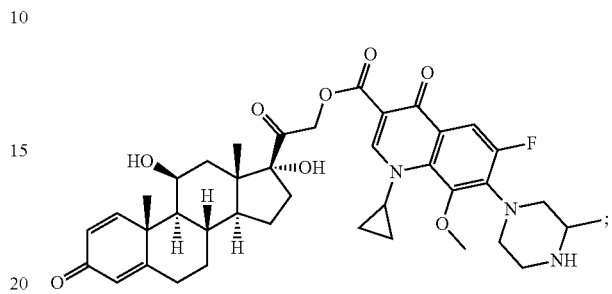

or a pharmaceutically acceptable salt thereof.

3. The hybrid drug of claim 2, wherein the pharmaceutically acceptable salt is a fumarate salt.

4. A method comprising administrating to an eye of a mammal a pharmaceutical composition comprising a therapeutically active amount of a hybrid drug of any one of claims 1-3, wherein said method is effective in the treatment of a bacterial infection or an inflammation affecting said eye.

5. The method according to claim 4, wherein the method is effective in the treatment of conjunctivitis, keratitis, blepharitis, dacryocystitis, hordeolum, corneal ulcers, anterior blepharitis, posterior blepharitis, endophthalmitis, meibomian gland dysfunction, dry eye disease, ocular pain, ocular pain and inflammation post-ocular surgery, bacterial conjunctivitis, anterior uveitis, post-surgical inflammation, inflammatory conditions of the palpebral and bulbar conjunctiva, cornea, and anterior segment of the globe, allergic conjunctivitis, ocular rosacea, blepharitis, meibomian gland dysfunction, superficial punctate keratitis, herpes zoster keratitis, iritis, cyclitis, selected infective conjunctivitis, corneal injury from chemical radiation, or thermal burns, penetration of foreign bodies or allergy.

6. The method according to claim 4, wherein the mammal is a human.

7. A pharmaceutical composition comprising a hybrid drug of claim 1 in a pharmaceutically acceptable carrier.

8. The hybrid drug of claim 1, wherein the covalent bond is an ester bond.

9. The pharmaceutical composition of claim 7, wherein said pharmaceutical composition is formulated for topical ophthalmic administration.

* * * * *